(12) United States Patent
Calos

(10) Patent No.: US 7,141,426 B2
(45) Date of Patent: *Nov. 28, 2006

(54) ALTERED RECOMBINASES FOR GENOME MODIFICATION

(75) Inventor: Michele P. Calos, Burlingame, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/836,323

(22) Filed: Apr. 29, 2004

(65) Prior Publication Data

US 2005/0003540 A1    Jan. 6, 2005

Related U.S. Application Data

(63) Continuation of application No. 09/788,297, filed on Feb. 16, 2001, now Pat. No. 6,808,925.

(60) Provisional application No. 60/183,759, filed on Feb. 18, 2000.

(51) Int. Cl.
*C12N 115/90* (2006.01)
*C12N 15/63* (2006.01)

(52) U.S. Cl. .................... 435/462; 435/320.1
(58) Field of Classification Search ............ 435/462, 435/320.1, 183
See application file for complete search history.

(56) References Cited

U.S. PATENT DOCUMENTS 5,817,491 A    10/1998 Yee et al.
5,888,732 A    3/1999 Hartley et al.

FOREIGN PATENT DOCUMENTS

WO    WO 02/38613    5/2002

OTHER PUBLICATIONS

Kuhstoss et al. "Analysis of the Integration Function of the Streptomycete bacteriophage ΦC31," (1991) *J. Mol. Biol*, 222:897-908.
Buchholz et al. "Improved Properties of FLP Recombinase Evolved by Cycling Mutagenesis," (1998) *Nature Biotechnology*, 16:657-662.
Christiansen et al. "A Resolvase-Like Protein is Required for the Site-Specific Integration of the Temperate Lactococcal bacteriophage TP901-1," (1996) *Journal of Bacteriology*, 178(17): 5164-5173.
Dorgai et al. "Identifying Determinants of Recombination Specificity: Construction and Characterization of Mutant Bacteriophage integrases," (1995) *J. Mol. Biol*, 252:178-188.
Hartung et al. "CRE Mutants with Altered DNA Binding Properties," (1998) *Journal of Biological Chemistry*, 273:22884-22891.

(Continued)

*Primary Examiner*—Nancy Vogel
(74) *Attorney, Agent, or Firm*—Edward J. Baba; Bret E. Field; Bozicevic, Field & Francis LLP

(57) ABSTRACT

The present invention describes methods of identifying altered recombinases and compositions thereof, wherein at least one amino acid is different from a parent, wild-type recombinase and the altered recombinase has improved recombination efficiency towards wild-type and/or pseudo att site sequences relative to the parent, wild-type recombinase. The present invention also includes methods of modifying the genomes of cells using the altered recombinases, including methods of site-specifically integrating a polynucleotide sequence of interest in a genome of a eucaryotic cell.

28 Claims, 15 Drawing Sheets

OTHER PUBLICATIONS

Matsuura et al. "The SRE Gene (ORF469) Encodes A Site-Specific Recombinase Responsible for Integration of the R4 Phage Genome," (1996) *Journal of Bacteriology*, 178(11)3374-3376.

Thorpe et al. "*In Vitro* Site-Specific Integration of Bacteriophage DNA Catalyzed by A Recombinase of the Resolvase/Invertase Family," (1998) *Proc. Natl. Acad. Sci. U.S.A.*, 95:5505-5510.

Verma et al. "Gene Therapy-Promises, Problems and Prospects," (1997) *Nature*, 389:239-242.

Palúet al. "In Pursuit of New Developments for Gene Therapy of Human Diseases," (1999) *J. Biotechnology*, 68:1-13.

Luo et al. "Synthetic DNA Delivery Systems," (2000) *Nature Biotechnology*, 18:33-37.

Fox "Gene Therapy Clinical Trials Raise Troubling Questions," (2000) *ASM News*, 66(2):1-3.

```
              1                                                           50
7C1 Mutant    ---------- ---------- ---------- ---------- ----------
WT PhiC31 Int ---------- ---------- ---------- ---------- ----------
5C1 Mutant    ---------- ---------- ---------- ---------- ----------
1C1 Mutant    ---------- ---------- ---------- ---------- ----------
Consensus     MTQGVVTGVD TYAGAYDRQS RERENSSAAS PATQRSANED KAADLQREVE 51                                                         100
7C1 Mutant    ---------- ---------- ---------- ---------- ----------
WT PhiC31 Int ---------- ---------- ---------- ---------- ----------
5C1 Mutant    ---------- ---------- ---------- ---------- ----------
1C1 Mutant    ---------- ---------- ---------- ---------- ----------
Consensus     RDGGRFRFVG HFSEAPGTSA FGTAERPEFE RILNECRAGR LNMIIVYDVS 101                                                        150
7C1 Mutant    ---------- ---------- ---------- ---------- ----------
WT PhiC31 Int ---------- ---------- ---------- ---------- ----------
5C1 Mutant    ---------- ---------- ---------- ---------- ----------
1C1 Mutant    ---------- ---------- ---------- ---------- ----------
Consensus     RFSRLKVMDA IPIVSELLAL GVTIVSTQEG VFRQGNVMDL IHLIMRLDAS 151                                                        200
7C1 Mutant    ---------- ---------- ---------- ---------- ----------
WT PhiC31 Int ---------- ---------- ---------- ---------- ----------
5C1 Mutant    ---------- ---------- ---------- ---------- ----------
1C1 Mutant    ---------- ---------- ---------- ---------- ----------
Consensus     HKESSLKSAK ILDTKNLQRE LGGYVGGKAP YGFELVSETK EITRNGRMVN 201                                                        250
7C1 Mutant    ---------- ---------- ---------- ---------- -----a----
WT PhiC31 Int ---------- ---------- ---------- ---------- -----a----
5C1 Mutant    ---------- ---------- ---------- ---------- -----t----
1C1 Mutant    ---------- ---------- ---------- ---------- -----a----
Consensus     VVINKLAHST TPLTGPFEFE PDVIRWWWRE IKTHKHLPFK PGSQA-IHPG 251                                                        300
7C1 Mutant    ---------- ---------- ---------- ---------- ----------
WT PhiC31 Int ---------- ---------- ---------- ---------- ----------
5C1 Mutant    ---------- ---------- ---------- ---------- ----------
1C1 Mutant    ---------- ---------- ---------- ---------- ----------
Consensus     SITGLCKRMD ADAVPTRGET IGKKTASSAW DPATVMRILR DPRIAGFAAE 301                                                        350
7C1 Mutant    ---------- ---------- ---------- ---------- ----------
WT PhiC31 Int ---------- ---------- ---------- ---------- ----------
5C1 Mutant    ---------- ---------- ---------- ---------- ----------
1C1 Mutant    ---------- ---------- ---------- ---------- ----------
Consensus     VIYKKKPDGT PTTKIEGYRI QRDPITLRPV ELDCGPIIEP AEWYELQAWL
```

FIG. 3A

```
              351                                                            400
7C1 Mutant    ----------  ---------d  --------v-  ----------  -----------
WT PhiC31 Int ----------  ---------d  --------v-  ----------  -----------
5C1 Mutant    ----------  ---------g  --------v-  ----------  -----------
1C1 Mutant    ----------  ---------d  --------i-  ----------  -----------
Consensus     DGRGRGKGLS  RGQAILSAM-  KLYCECGA-M  TSKRGEESIK  DSYRCRRRKV 401                                                            450
7C1 Mutant    ----------  ----------  ----------  ----------  -----------
WT PhiC31 Int ----------  ----------  ----------  ----------  -----------
5C1 Mutant    ----------  ----------  ----------  ----------  -----------
1C1 Mutant    ----------  ----------  ----------  ----------  -----------
Consensus     VDPSAPGQHE  GTCNVSMAAL  DKFVAERIFN  KIRHAEGDEE  TLALLWEAAR 451                                                            500
7C1 Mutant    ----------  ----------  ----------  ----------  -----------
WT PhiC31 Int ----------  ----------  ----------  ----------  -----------
5C1 Mutant    ----------  ----------  ----------  ----------  -----------
1C1 Mutant    ----------  ----------  ----------  ----------  -----------
Consensus     RFGKLTEAPE  KSGERANLVA  ERADALNALE  ELYEDRAAGA  YDGPVGRKHF 501                                                            550
7C1 Mutant    ----------  ----------  ----------  ----------  -----------
WT PhiC31 Int ----------  ----------  ----------  ----------  -----------
5C1 Mutant    ----------  ----------  ----------  ----------  -----------
1C1 Mutant    ----------  ----------  ----------  ----------  -----------
Consensus     RKQQAALTLR  QQGAEERLAE  LEAAEAPKLP  LDQWFPEDAD  ADPTGPKSWW 551                                                            600
7C1 Mutant    ---------m  ----------  ----------  ----------  -----------
WT PhiC31 Int ---------v  ----------  ----------  ----------  -----------
5C1 Mutant    ---------v  ----------  ----------  ----------  -----------
1C1 Mutant    ---------v  ----------  ----------  ----------  -----------
Consensus     GRASVDDKR-  FVGLFVDKIV  VTKSTTGRGQ  GTPIEKRASI  TWAKPPTDDD 601         614
7C1 Mutant    ----qdgtqd  vaa*
WT PhiC31 Int ----qdgted  vaa*
5C1 Mutant    ----qdgted  vaa*
1C1 Mutant    ----rtarkt  *---
Consensus     EDDA------  ----
```

FIG. 3B

DNA Sequence of ΦC31 Integrase

```
ATGacacaaggggttgtgaccggggtggacacgtacgcgggtgcttacgaccgtcagtcgcgcg
agcgcgaaaattcgagcgcagcaagcccagcgacacagcgtagcgccaacgaagacaaggcggc
cgaccttcagcgcgaagtcgagcgcgacggggccggttcaggttcgtcgggcatttcagcgaa
gcgccgggcacgtcggcgttcgggacggcggagcgcccggagttcgaacgcatcctgaacgaat
gccgcgccgggcggctcaacatgatcattgtctatgacgtgtcgcgcttctcgcgcctgaaggt
catggacgcgattccgattgtctcggaattgctcgccctgggcgtgacgattgtttccactcag
gaaggcgtcttccggcagggaaacgtcatggacctgattcacctgattatgcggctcgacgcgt
cgcacaaagaatcttcgctgaagtcggcgaagattctcgacacgaagaaccttcagcgcgaatt
gggcgggtacgtcggcgggaaggcgccttacggcttcgagcttgtttcggagacgaaggagatc
acgcgcaacggccgaatggtcaatgtcgtcatcaacaagcttgcgcactcgaccactcccctta
ccggacccttcgagttcgagcccgacgtaatccggtggtggtggcgtgagatcaagacgcacaa
acaccttcccttcaagccgggcagtcaagccgccattcacccgggcagcatcacggggctttgt
aagcgcatggacgctgacgccgtgccgacccggggcgagacgattgggaagaagaccgcttcaa
gcgcctgggacccggcaaccgttatgcgaatccttcgggacccgcgtattgcgggcttcgccgc
tgaggtgatctacaagaagaagccggacggcacgccgaccacgaagattgagggttaccgcatt
cagcgcgacccgatcacgctccggccggtcgagcttgattgcggaccgatcatcgagcccgctg
agtggtatgagcttcaggcgtggttggacggcagggggcgcggcaaggggctttcccgggggca
agccattctgtccgccatggacaagctgtactgcgagtgtggcgccgtcatgacttcgaagcgc
ggggaagaatcgatcaaggactcttaccgctgccgtcgccggaaggtggtcgacccgtccgcac
ctgggcagcacgaaggcacgtgcaacgtcagcatggcggcactcgacaagttcgttgcggaacg
catcttcaacaagatcaggcacgccgaaggcgacgaagagacgttggcgcttctgtgggaagcc
gcccgacgcttcggcaagctcactgaggcgcctgagaagagcggcgaacgggcgaaccttgttg
cggagcgcgccgacgccctgaacgcccttgaagagctgtacgaagaccgcgcggcaggcgcgta
cgacggacccgttggcaggaagcacttccggaagcaacaggcagcgctgacgctccggcagcaa
ggggcggaagagcggcttgccgaacttgaagccgccgaagccccgaagcttccccttgaccaat
ggttccccgaagacgccgacgctgacccgaccggccctaagtcgtggtggggcgcgcgtcagt
agacgacaagcgcgtgttcgtcgggctcttcgtagacaagatcgttgtcacgaagtcgactacg
ggcaggggggcagggaacgcccatcgagaagcgcgcttcgatcacgtgggcgaagccgccgaccg
acgacgaagacgacgcccaggacggcacggaagacgtagcggcgtag
```

(SEQ ID NO:20)

FIG. 4

Peptide sequence of the ΦC31 mutant integrase 7C1

```
  1  MTQGVVTGVD TYAGAYDRQS RERENSSAAS PATQRSANED KAADLQREVE
 51  RDGGRFRFVG HFSEAPGTSA FGTAERPEFE RILNECRAGR LNMIIVYDVS
101  RFSRLKVMDA IPIVSELLAL GVTIVSTQEG VFRQGNVMDL IHLIMRLDAS
151  HKESSLKSAK ILDTKNLQRE LGGYVGGKAP YGFELVSETK EITRNGRMVN
201  VVINKLAHST TPLTGPFEFE PDVIRWWWRE IKTHKHLPFK PGSQAAIHPG
251  SITGLCKRMD ADAVPTRGET IGKKTASSAW DPATVMRILR DPRIAGFAAE
301  VIYKKKPDGT PTTKIEGYRI QRDPITLRPV ELDCGPIIEP AEWYELQAWL
351  DGRGRGKGLS RGQAILSAMD KLYCECGAVM TSKRGEESIK DSYRCRRRKV
401  VDPSAPGQHE GTCNVSMAAL DKFVAERIFN KIRHAEGDEE TLALLWEAAR
451  RFGKLTEAPE KSGERANLVA ERADALNALE ELYEDRAAGA YDGPVGRKHF
501  RKQQAALTLR QQGAEERLAE LEAAEAPKLP LDQWFPEDAD ADPTGPKSWW
551  GRASVDDKRM FVGLFVDKIV VTKSTTGRGQ GTPIEKRASI TWAKPPTDDD
601  EDDAQDGTQD VAA*
```

(SEQ ID NO:22)

FIG. 5

DNA Sequence of Integrase mutant 7C1

ATGacacaaggggttgtgaccggggtggacacgtacgcgggtgcttacgaccgtcagtcgcgcg
agcgcgaaaattcgagcgcagcaagcccagcgacacagcgtagcgccaacgaagacaaggcggc
cgaccttcagcgcgaagtcgagcgcgacggggggccggttcaggttcgtcgggcatttcagcgaa
gcgccgggcacgtcggcgttcgggacggcggagcgcccggagttcgaacgcatcctgaacgaat
gccgcgccgggcggctcaacatgatcattgtctatgacgtgtcgcgcttctcgcgcctgaaggt
catggacgcgattccgattgtctcggaattgctcgccctgggcgtgacgattgtttccactcag
gaaggcgtcttccggcagggaaacgtcatggacctgattcacctgattatgcggctcgacgcgt
cgcacaaagaatcttcgctgaagtcggcgaagattctcgacacgaagaaccttcagcgcgaatt
gggcgggtacgtcggcgggaaggcgccttacggcttcgagcttgtttcggagacgaaggagatc
acgcgcaacggccgaatggtcaatgtcgtcatcaacaagcttgcgcactcgaccactcccctta
ccggacccttcgagttcgagcccgacgtaatccggtggtggtggcgtgagatcaagacgcacaa
acaccttcccttcaagccgggcagtcaagccgccattcacccgggcagcatcacggggctttgt
aagcgcatggacgctgacgccgtgccgacccggggcgagacgattgggaagaagaccgcttcaa
gcgcctgggacccggcaaccgttatgcgaatccttcgggacccgcgtatCgcgggcttcgccgc
tgaggtgatctacaagaagaagccggacggcacgccgaccacgaagattgagggttaccgcatt
cagcgcgacccgatcacgctccggccggtcgagcttgattgcggaccgatcatcgagcccgctg
agtggtatgagcttcaggcgtggttggacggcaggggggcgcggcaaggggctttcccggggca
agccattctgtccgccatggacaagctgtactgcgagtgtggcgccgtcatgacttcgaagcgc
ggggaagaatcgatcaaggactcttaccgctgccgtcgccggaaggtggtcgacccgtccgcac
ctgggcagcacgaaggcacgtgcaacgtcagcatggcggcactcgacaagttcgttgcggaacg
catcttcaacaagatcaggcacgccgaaggcgacgaagagacgttggcgcttctgtgggaagcc
gcccgacgcttcggcaagctcactgaggcgcctgagaagagcggcgaacgggcgaaccttgttg
cggagcgcgccgacgccctgaacgcccttgaagagctgtacgaagaccgcgcggcaggcgcgta
cgacggacccgttggcaggaagcacttccggaagcaacaggcagcgctgacgctccggcagcaa
ggggcggaagagcggcttgccgaacttgaagccgccgaagccccgaagcttccccttgaccaat
ggttccccgaagacgccgacgctgacccgaccggccctaagtcgtggtggggcgcgcgtcagt
agacgacaagcgcAtgttcgtcgggctcttcgtagacaagatcgttgtcacgaagtcgactacg
ggcaggggcagggaacgcccatcgagaagcgcgcttcgatcacgtgggcgaagccgccgaccg
acgacgacgaagacgacgcccaggacggcacgCaagacgtagcggcgtag (SEQ ID NO:26)

FIG. 6

Peptide sequence of the ΦC31 mutant integrase 5C1

```
  1  MTQGVVTGVD TYAGAYDRQS RERENSSAAS PATQRSANED KAADLQREVE
 51  RDGGRFRFVG HFSEAPGTSA FGTAERPEFE RILNECRAGR LNMIIVYDVS
101  RFSRLKVMDA IPIVSELLAL GVTIVSTQEG VFRQGNVMDL IHLIMRLDAS
151  HKESSLKSAK ILDTKNLQRE LGGYVGGKAP YGFELVSETK EITRNGRMVN
201  VVINKLAHST TPLTGPFEFE PDVIRWWWRE IKTHKHLPFK PGSQATIHPG
251  SITGLCKRMD ADAVPTRGET IGKKTASSAW DPATVMRILR DPRIAGFAAE
301  VIYKKKPDGT PTTKIEGYRI QRDPITLRPV ELDCGPIIEP AEWYELQAWL
351  DGRGRGKGLS RGQAILSAMG KLYCECGAVM TSKRGEESIK DSYRCRRRKV
401  VDPSAPGQHE GTCNVSMAAL DKFVAERIFN KIRHAEGDEE TLALLWEAAR
451  RFGKLTEAPE KSGERANLVA ERADALNALE ELYEDRAAGA YDGPVGRKHF
501  RKQQAALTLR QQGAEERLAE LEAAEAPKLP LDQWFPEDAD ADPTGPKSWW
551  GRASVDDKRV FVGLFVDKIV VTKSTTGRGQ GTPIEKRASI TWAKPPTDDD
601  EDDAQDGTED VAA*
```

(SEQ ID NO:23)

FIG. 7

DNA Sequence of Integrase mutant 5C1

ATGacacaaggggttgtgaccggggtggacacgtacgcgggtgcttacgaccgtcagtcgcgcg
agcgcgaaaattcgagcgcagcaagcccagcgacacagcgtagcgccaacgaagacaaggcggc
cgaccttcagcgcgaagtcgagcgcgacgggggccggttcagAttcgtcgggcatttcagcgaa
gcgccgggcacgtcggcgttcgggacggcggagcgcccggagttcgaacgcatcctgaacgaat
gccgcgccgggcggctcaacatgatcattgtctatgacgtgtcgcgcttctcgcgcctgaaggt
catggacgcgattccgattgtctcggaattgctcgccctgggcgtgacgattgtttccactcag
gaaggcgtcttccggcagggaaacgtcatggacctgattcacctgattatgcggctcgacgcgt
cgcacaaagaatcttcgctgaagtcggcgaagattctcgacacgaagaaccttcagcgcgaatt
gggcgggtacgtcggcgggaaggcgccttacggcttcgagcttgtttcggagacgaaggagatc
acgcgcaacggccgaatggtcaatgtcgtcatcaacaagcttgcgcactcgaccactcccctta
ccggacccttcgagttcgagcccgacgtaatccggtggtggtggcgtgagatcaagacgcacaa
acaccttcccttcaagccgggcagtcaagccAccattcacccggggcagcatcacggggctttgt
aagcgcatggacgctgacgccgtgccgacccggggcgagacgattgggaagaagaccgcttcaa
gcgcctgggacccggcaaccgttatgcgaatccttcgggacccgcgtattgcgggcttcgccgc
tgaggtgatctacaagaagaagccggacggcacgccgaccacgaagattgagggttaccgcatt
cagcgcgacccgatcacgctccggccggtcgagcttgattgcggaccgatcatcgagcccgctg
agtggtatgagcttcaggcgtggttggacggcaggggggcgcggcaaggggctttcccgggggca
agccattctgtccgccatggCaagctgtactgcgagtgtggcgccgtcatgacttcgaagcgc
ggggaagaatcgatcaaggactcttaccgctgccgtcgccggaaggtggtcgacccgtccgcac
ctgggcagcacgaaggcacgtgcaacgtcagcatggcggcactcgacaagttcgttgcggaacg
catcttcaacaagatcaggcacgccgaaggcgacgaagagacgttggcgcttctgtgggaagcc
gcccgacgcttcggcaagctcactgaggcgcctgagaagagcggcgaacgggcgaaccttgttg
cggagcgcgccgacgccctgaacgcccttgaagagctgtacgaagaccgcgcggcaggcgcgta
cgacggacccgttggcaggaagcacttccggaagcaacaggcagcgctgacgctccggcagcaa
ggggcggaagagcggcttgccgaacttgaagccgccgaagccccgaagcttccccttgaccaat
ggttccccgaagacgccgacgctgacccgaccggccctaagtcgtggtggggcgcgcgtcagt
agacgacaagcgcgtgttcgtcgggctcttcgtagacaagatcgttgtcacgaagtcgactacg
ggcaggggcagggaacgcccatcgagaagcgcgcttcgatcacgtgggcgaagccgccAaccg
acgacgacgaagacgacgcccaggacggcacggaagacgtagcggcg (SEQ ID NO:27)

FIG. 8

Peptide sequence of the ΦC31 mutant integrase 1C1

```
  1  MTQGVVTGVD TYAGAYDRQS RERENSSAAS PATQRSANED KAADLQREVE
 51  RDGGRFRFVG HFSEAPGTSA FGTAERPEFE RILNECRAGR LNMIIVYDVS
101  RFSRLKVMDA IPIVSELLAL GVTIVSTQEG VFRQGNVMDL IHLIMRLDAS
151  HKESSLKSAK ILDTKNLQRE LGGYVGGKAP YGFELVSETK EITRNGRMVN
201  VVINKLAHST TPLTGPFEFE PDVIRWWWRE IKTHKHLPFK PGSQAAIHPG
251  SITGLCKRMD ADAVPTRGET IGKKTASSAW DPATVMRILR DPRIAGFAAE
301  VIYKKKPDGT PTTKIEGYRI QRDPITLRPV ELDCGPIIEP AEWYELQAWL
351  DGRGRGKGLS RGQAILSAMD KLYCECGAIM TSKRGEESIK DSYRCRRRKV
401  VDPSAPGQHE GTCNVSMAAL DKFVAERIFN KIRHAEGDEE TLALLWEAAR
451  RFGKLTEAPE KSGERANLVA ERADALNALE ELYEDRAAGA YDGPVGRKHF
501  RKQQAALTLR QQGAEERLAE LEAAEAPKLP LDQWFPEDAD ADPTGPKSWW
551  GRASVDDKRV FVGLFVDKIV VTKSTTGRGQ GTPIEKRASI TWAKPPTDDD
601  EDDARTARKT *
```

(SEQ ID NO:24)

FIG. 9

DNA Sequence of Integrase mutant 1C1

ATGacacaaggggttgtgaccggggtggacacgtacgcgggtgcttacgaccgtcagtcgcgcg
agcgcgaaaattcgagcgcagcaagcccagcgacacagcgtagcgccaacgaagacaaggcggc
cgaccttcagcgcgaagtcgagcgcgacgggggccggttcaggttcgtcgggcatttcagcgaa
gcgccgggcacgtcggcgttcgggacggcggaAcgcccggagttcgaacgcatcctgaacgaat
gccgcgccgggcggctcaacatgatcattgtctatgacgtgtcgcgcttctcgcgcctgaaggt
catggacgcgattccgattgtctcggaattgctcgccctgggcgtgacgattgtttccactcag
gaaggcgtcttccggcagggaaacgtcatggacctgattcacctgattatgcggctcgacgcgt
cgcacaaagaatcttcgctgaagtcggcgaagattctcgacacgaagaaccttcagcgcgaaCt
gggcgggtacgtcggcgggaaggcgccttacggcttcgagcttgtttcggagacgaaggagatc
acgcgcaacggccgaatggtcaatgtcgtcatcaacaagcttgcgcactcgaccactcccctta
ccggacccttcgagttcgagcccgacgtaatccggtggtggtggcgtgagatcaagacgcacaa
acaccttcccttcaagccgggcagtcaagccgccattcacccgggcagcatcacggggctttgt
aagcgcatggacgctgacgccgtgccgacccggggcgagacgattgggaagaagaccgcttcaa
gcgcctgggacccggcaaccgttatgcgaatccttcgggacccgcgtattgcgggcttcgccgc
tgaggtgatctacaagaagaagccggacggcacgccgaccacgaagattgagggttaccgcatt
cagcgcgacccgatcacgctccggccggtcgagcttgattgcggaccgatcatcgagcccgctg
agtggtatgagcttcaggcgtggttggacggcaggggcgcggcaaggggctttccgggggca
agccattctgtccgccatggacaagctgtactgcgagtgtggcgccAtcatgacttcgaagcgc
ggggaagaatcgatcaaggactcttaccgctgccgtcgccggaaggtggtcgacccgtccgcac
ctgggcagcacgaaggcacgtgcaacgtcagcatggcggcactcgacaagttcgttgcggaacg
catcttcaacaagatcaggcacgccgaaggcgacgaagagacgttggcgcttctgtgggaagcc
gcccgacgcttcggcaagctcactgaggcgcctgagaagagcggcgaacgggcgaaccttgttg
cggagcgcgccgacgccctgaacgcccttgaagagctgtacgaagaccgcgcggcaggcgcgta
cgacggacccgttggcaggaagcacttccggaagcaGcaggcagcgctgacgctccggcagcaa
ggggcggaagagcggcttgccgaacttgaagccgccgaagccccgaagcttccccttgaccaat
ggttccccgaagacgccgacgctgacccgaccggccctaagtcgtggtgggggcgcgcgtcagt
agacgacaagcgcgtgttcgtcgggctcttcgtagacaagatTgttgtcacgaagtcgactacg
ggcaggggcagggaacgcccatcgagaagcgcgcttcgatcacgtgggcgaagccgccgaccg
acgacgacgaagacgacg:ccaggacggcacggaagacgtag (SEQ ID NO:28)

FIG. 10

Full Length ΦC31 attP Site ccggtactgacggacacaccgaagccccggcggcaaccctcagcggatgccccggggcttcacg
ttttcccaggtcagaagcggttttcggga gtagtgccccaactggggtaacctTTGagttctct
cagttgggggcgtagggtcgccgacatgacacaaggggttgtgaccggggtggacacgtacgcg
ggtgcttacgaccgtcagtcgcggcc (SEQ ID NO:29)

FIG. 11A

Full length ΦC31 attB Site cgatgtaggtcacggtctcgaagccgcggtgcgggtgccagggcgtgcccTTGggctccccggg
cgcgtactccacctcacccatctggtccatcatgatgaacgggtcgaggtggcggtagttgatc
ccggcgaacgcgcggcgcaccgggaagccctcgccctcgaaaccgctgggcgcggtggtcacgg
tgagcacgggacgtgcgacggcgtcggcgggtgcggatacgcggggcagcgtcagcgggttctc
gacggtcacggcgggcatgtcga (SEQ ID NO:30)

FIG. 11B

A 59 bp wild-type φC31 attP site ggagtagtgccccaactggggtaacctTTGagttctctcagttgggggcgtagggtcgc (SEQ ID NO:33)

FIG. 11C

R4 attB295 with core underlined

CGTGGGGACGCCGTACAGGGACGTGCACCTCTCCCGCTGCACCGCCTCCAGCGTCGC
CGCCGGCTCGAAGGACGGGGCCGGGATGACGATGCAGGCGGCGTGGGAGGTGGCG
CCCAAGTTGCCCATGACCATGCC<u>GAAGCAGTGGTA</u>GAAGGGCACCGGCAGACACAC
CCGGTCCTGCTCCGTGTAGCCGACCGTGCGGCCCACCCAGTAGCCGTTGTTGAGGAT
GTTGTGGTGGGAGAGCGTGGCGCCCTTGGGGAAGCCGGTGGTGCCGGAGGTGTACT
GGATGTTGACCGGG (SEQ ID NO:31)

FIG. 12A

R4 attP64 with core underlined

GCATGTTCCCCAAAGCGATACCACTT<u>GAAGCAGTGGTA</u>CTGCTTGTGGGTACACTCT
GCGGGTG (SEQ ID NO:32)

FIG. 12B

DNA Sequence of ΨA

```
atttgtagaactattatgggacttaaaggggatatgggaggccacagttgagatg
ccttccaatcagaggcttggtgagattccaagaggtggtttcaaatacagcaata
agtacttgggtttcccTTGgtgtccccatggagattttaagccatgacgcaatgt
ttaaatcagagtggtatttttatgacttaagcgggtaaatatgcaattggaaaat
attcagggaagggtgatttggtccagaagagtgggggcatccagagtacagtggg
tgaaatggatcggacttttggaagagagccttgtgctggacaggatggtccagt
attgtcaacacaagtttctcatgcttcactctccttcctagcaacaggaagacgg
aaatgaggccatgcaaaaataaaagaccctgaaagactccagacaatacctgatc
caccctaccattcacctgtatagccagaagactt
```

(SEQ ID NO:34)

FIG. 13

SEQUENCE LISTING

```
<160> NUMBER OF SEQ ID NOS: 34

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence:Linker 1

<400> SEQUENCE: 1
cgcgtggtgc ttgcttagcg ctagcgcatg c                                    31

<210> SEQ ID NO 2
<211> LENGTH: 72
<212> TYPE: DNA
<213> ORGANISM: Artificial Sequence
<220> FEATURE:
<223> OTHER INFORMATION: Description of Artificial Sequence:Linker 2,
      first oligonucleotide
```

-continued

```
<400> SEQUENCE: 2
cgcgtgacgt caaaaccggt gcggccgcga attccggtcc gaaacctagg aaactgcagg      60
gcgcgccaaa gc                                                          72

<210> SEQ ID NO 3
<211> LENGTH: 71
<212> TYPE: DNA
<213> ORGANISM: Artificial Sequence
<220> FEATURE:
<223> OTHER INFORMATION: Description of Artificial Sequence:Linker 2,
      second oligonucleotide

<400> SEQUENCE: 3
taagctttgg cgcgccctgc agtttcctag gtttcggacc ggaattcgcg gccgcaccgg      60
ttttgacgtc a                                                           71

<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence:Linker 3,
      first oligonucleotide

<400> SEQUENCE: 4
ggggtttaaa cggg                                                        14

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence:Linker 3,
      second oligonucleotide

<400> SEQUENCE: 5
cccgtttaaa cccc                                                        14

<210> SEQ ID NO 6
<211> LENGTH: 72
<212> TYPE: DNA
<213> ORGANISM: Artificial Sequence
<220> FEATURE:
<223> OTHER INFORMATION: Description of Artificial Sequence:T5, oligo 1

<400> SEQUENCE: 6
ctcataaaaa atttatttgc tttcaggaaa attttctgt ataatagatt cataaatttg       60
agagaggagt ta                                                          72

<210> SEQ ID NO 7
<211> LENGTH: 80
<212> TYPE: DNA
<213> ORGANISM: Artificial Sequence
<220> FEATURE:
<223> OTHER INFORMATION: Description of Artificial Sequence:T5, oligo 2

<400> SEQUENCE: 7
ccggtaactc ctctctcaaa tttatgaatc tattatacag aaaaattttc ctgaaagcaa      60
ataaattttt tatgagacgt                                                  80

<210> SEQ ID NO 8
<211> LENGTH: 52
<212> TYPE: DNA
```

<213> ORGANISM: Artificial Sequence
<220> FEATURE:
<223> OTHER INFORMATION: Description of Artificial Sequence:
      transcription terminator, oligo 1

<400> SEQUENCE: 8
gtccgtggat tgttcagaa cgctcggttg ccgccgggcg tttttttattg gc         52

<210> SEQ ID NO 9
<211> LENGTH: 53
<212> TYPE: DNA
<213> ORGANISM: Artificial Sequence
<220> FEATURE:
<223> OTHER INFORMATION: Description of Artificial Sequence:
      transcription terminator, oligo 2

<400> SEQUENCE: 9
ctaggccaat aaaaaacgcc cggcggcaac cgagcgttct gaacaaatcc acg        53

<210> SEQ ID NO 10
<211> LENGTH: 53
<212> TYPE: DNA
<213> ORGANISM: Artificial Sequence
<220> FEATURE:
<223> OTHER INFORMATION: Description of Artificial Sequence:attB, oligo
      1

<400> SEQUENCE: 10
cgcgcctgcg ggtgccaggg cgtgcccttg ggctccccgg gcgcgtactc cgg        53

<210> SEQ ID NO 11
<211> LENGTH: 53
<212> TYPE: DNA
<213> ORGANISM: Artificial Sequence
<220> FEATURE:
<223> OTHER INFORMATION: Description of Artificial Sequence:attB, oligo
      2

<400> SEQUENCE: 11
cgcgccggag tacgcgcccg gggagcccaa gggcacgccc tggcacccgc agg        53

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:primer 1

<400> SEQUENCE: 12
cgttgggacc cgtttccgtg                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:primer 2

<400> SEQUENCE: 13
agagacgagg agaggggagc                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:psiA primer -continued

<400> SEQUENCE: 14
atttgtagaa ctattatggg                                               20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:psiA primer
      2

<400> SEQUENCE: 15
aagtcttctg gctatacagg                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:linker 4,
      first oligo

<400> SEQUENCE: 16
gtcacgctcg agagatctga                                               20

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence:linker 4,
      second oligo

<400> SEQUENCE: 17
ctagtcagat ctctcgagc                                                19

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence:phiC31
      primer 1

<400> SEQUENCE: 18
ctaaagggaa caaaagctgg ag                                            22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence:phiC31
      primer 2

<400> SEQUENCE: 19
tgatatgggg caaatggtgg tc                                            22

<210> SEQ ID NO 20
<211> LENGTH: 1842
<212> TYPE: DNA
<213> ORGANISM: Phage phiC31

<400> SEQUENCE: 20

-continued

```
atgacacaag gggttgtgac cggggtggac acgtacgcgg gtgcttacga ccgtcagtcg      60
cgcgagcgcg aaaattcgag cgcagcaagc ccagcgacac agcgtagcgc aacgaagac      120
aaggcggccg accttcagcg cgaagtcgag cgcgacgggg gccggttcag gttcgtcggg     180
catttcagcg aagcgccggg cacgtcggcg ttcgggacgg cggagcgccc ggagttcgaa     240
cgcatcctga cgaatgccg cgccgggcgg ctcaacatga tcattgtcta tgacgtgtcg      300
cgcttctcgc gcctgaaggt catggacgcg attccgattg tctcggaatt gctcgccctg     360
ggcgtgacga ttgttccac tcaggaaggc gtcttccggc agggaaacgt catggacctg      420
attcacctga ttatgcggct cgacgcgtcg cacaaagaat cttcgctgaa gtcggcgaag     480
attctcgaca cgaagaacct tcagcgcgaa ttgggcgggt acgtcggcgg aaggcgcct      540
tacggcttcg agcttgtttc ggagacgaag gagatcacgc gcaacggccg aatggtcaat    600
gtcgtcatca acaagcttgc gcactcgacc actcccctta ccggaccctt cgagttcgag    660
cccgacgtaa tccggtggtg gtggcgtgag atcaagacgc acaaacacct tcccttcaag    720
ccgggcagtc aagccgccat tcacccgggc agcatcacgg ggctttgtaa cgcatggac     780
gctgacgccg tgccgacccg gggcgagacg attgggaaga gaccgcttc aagcgcctgg     840
gacccggcaa ccgttatgcg aatccttcgg gacccgcgta ttgcgggctt cgccgctgag    900
gtgatctaca agaagaagcc ggacggcacg ccgaccacga agattgaggg ttaccgcatt    960
cagcgcgacc cgatcacgct ccggccggtc gagcttgatt gcggaccgat catcgagccc  1020
gctgagtggt atgagcttca ggcgtggttg gacggcaggg ggcgcggcaa ggggctttcc    1080
cgggggcaag ccattctgtc cgccatggac aagctgtact gcgagtgtgg cgccgtcatg    1140
acttcgaagc gcggggaaga atcgatcaag gactcttacc gctgccgtcg ccggaaggtg    1200
gtcgacccgt ccgcacctgg gcagcacgaa ggcacgtgca acgtcagcat ggcggcactc    1260
gacaagttcg ttgcggaacg catcttcaac aagatcaggc acgccgaagg cgacgaagag    1320
acgttggcgc ttctgtggga agccgcccga cgcttcggca agctcactga ggcgcctgag    1380
aagagcggcg aacgggcgaa ccttgttgcg gagcgcgccg acgccctgaa cgcccttgaa    1440
gagctgtacg aagaccgcgc ggcaggcgcg tacgacggac ccgttggcag gaagcacttc    1500
cggaagcaac aggcagcgct gacgctccgg cagcaagggg cggaagagcg gcttgccgaa    1560
cttgaagccg ccgaagcccc gaagcttccc cttgaccaat ggttcccga agacgccgac     1620
gctgacccga ccggccctaa gtcgtggtgg gggcgcgcgt cagtagacga caagcgcgtg    1680
ttcgtcgggc tcttcgtaga caagatcgtt gtcacgaagt cgactacggg caggggcag    1740
ggaacgccca tcgagaagcg cgcttcgatc acgtgggcga agccgccgac cgacgacgac    1800
gaagacgacg cccaggacgg cacggaagac gtagcggcgt ag                       1842
```

<210> SEQ ID NO 21
<211> LENGTH: 613
<212> TYPE: PRT
<213> ORGANISM: Phage phiC31

<400> SEQUENCE: 21

Met Thr Gln Gly Val Val Thr Gly Val Asp Thr Tyr Ala Gly Ala Tyr
1               5                   10                  15

Asp Arg Gln Ser Arg Glu Arg Glu Asn Ser Ser Ala Ala Ser Pro Ala
            20                  25                  30

Thr Gln Arg Ser Ala Asn Glu Asp Lys Ala Ala Asp Leu Gln Arg Glu
        35                  40                  45

```
Val Glu Arg Asp Gly Gly Arg Phe Arg Phe Val Gly His Phe Ser Glu
 50                  55                  60
Ala Pro Gly Thr Ser Ala Phe Gly Thr Ala Glu Arg Pro Glu Phe Glu
 65                  70                  75                  80
Arg Ile Leu Asn Glu Cys Arg Ala Gly Arg Leu Asn Met Ile Ile Val
                 85                  90                  95
Tyr Asp Val Ser Arg Phe Ser Arg Leu Lys Val Met Asp Ala Ile Pro
                100                 105                 110
Ile Val Ser Glu Leu Leu Ala Leu Gly Val Thr Ile Val Ser Thr Gln
            115                 120                 125
Glu Gly Val Phe Arg Gln Gly Asn Val Met Asp Leu Ile His Leu Ile
130                 135                 140
Met Arg Leu Asp Ala Ser His Lys Glu Ser Ser Leu Lys Ser Ala Lys
145                 150                 155                 160
Ile Leu Asp Thr Lys Asn Leu Gln Arg Glu Leu Gly Gly Tyr Val Gly
                165                 170                 175
Gly Lys Ala Pro Tyr Gly Phe Glu Leu Val Ser Glu Thr Lys Glu Ile
            180                 185                 190
Thr Arg Asn Gly Arg Met Val Asn Val Ile Asn Lys Leu Ala His
        195                 200                 205
Ser Thr Thr Pro Leu Thr Gly Pro Phe Glu Phe Glu Pro Asp Val Ile
210                 215                 220
Arg Trp Trp Arg Glu Ile Lys Thr His Lys His Leu Pro Phe Lys
225                 230                 235                 240
Pro Gly Ser Gln Ala Ala Ile His Pro Gly Ser Ile Thr Gly Leu Cys
                245                 250                 255
Lys Arg Met Asp Ala Asp Ala Val Pro Thr Arg Gly Glu Thr Ile Gly
            260                 265                 270
Lys Lys Thr Ala Ser Ser Ala Trp Asp Pro Ala Thr Val Met Arg Ile
        275                 280                 285
Leu Arg Asp Pro Arg Ile Ala Gly Phe Ala Ala Glu Val Ile Tyr Lys
290                 295                 300
Lys Lys Pro Asp Gly Thr Pro Thr Thr Lys Ile Glu Gly Tyr Arg Ile
305                 310                 315                 320
Gln Arg Asp Pro Ile Thr Leu Arg Pro Val Glu Leu Asp Cys Gly Pro
                325                 330                 335
Ile Ile Glu Pro Ala Glu Trp Tyr Glu Leu Gln Ala Trp Leu Asp Gly
            340                 345                 350
Arg Gly Arg Gly Lys Gly Leu Ser Arg Gly Gln Ala Ile Leu Ser Ala
        355                 360                 365
Met Asp Lys Leu Tyr Cys Glu Cys Gly Ala Val Met Thr Ser Lys Arg
370                 375                 380
Gly Glu Glu Ser Ile Lys Asp Ser Tyr Arg Cys Arg Arg Lys Val
385                 390                 395                 400
Val Asp Pro Ser Ala Pro Gly Gln His Glu Gly Thr Cys Asn Val Ser
                405                 410                 415
Met Ala Ala Leu Asp Lys Phe Val Ala Glu Arg Ile Phe Asn Lys Ile
            420                 425                 430
Arg His Ala Glu Gly Asp Glu Glu Thr Leu Ala Leu Leu Trp Glu Ala
        435                 440                 445
Ala Arg Arg Phe Gly Lys Leu Thr Glu Ala Pro Glu Lys Ser Gly Glu
450                 455                 460
Arg Ala Asn Leu Val Ala Glu Arg Ala Asp Ala Leu Asn Ala Leu Glu
```

-continued

```
                465                 470                 475                 480
Glu Leu Tyr Glu Asp Arg Ala Ala Gly Ala Tyr Asp Gly Pro Val Gly
                    485                 490                 495

Arg Lys His Phe Arg Lys Gln Gln Ala Ala Leu Thr Leu Arg Gln Gln
                500                 505                 510

Gly Ala Glu Glu Arg Leu Ala Glu Leu Glu Ala Ala Glu Ala Pro Lys
            515                 520                 525

Leu Pro Leu Asp Gln Trp Phe Pro Glu Asp Ala Asp Ala Asp Pro Thr
        530                 535                 540

Gly Pro Lys Ser Trp Trp Gly Arg Ala Ser Val Asp Lys Arg Val
545                 550                 555                 560

Phe Val Gly Leu Phe Val Asp Lys Ile Val Thr Lys Ser Thr Thr
                565                 570                 575

Gly Arg Gly Gln Gly Thr Pro Ile Glu Lys Arg Ala Ser Ile Thr Trp
                580                 585                 590

Ala Lys Pro Pro Thr Asp Asp Glu Asp Ala Gln Asp Gly Thr
            595                 600                 605

Glu Asp Val Ala Ala
    610
```

<210> SEQ ID NO 22
<211> LENGTH: 613
<212> TYPE: PRT
<213> ORGANISM: Artificial Sequence
<220> FEATURE:
<223> OTHER INFORMATION: Description of Artificial Sequence:altered recombinase 7C1

<400> SEQUENCE: 22

```
Met Thr Gln Gly Val Val Thr Gly Val Asp Thr Tyr Ala Gly Ala Tyr
1               5                   10                  15

Asp Arg Gln Ser Arg Glu Arg Glu Asn Ser Ser Ala Ala Ser Pro Ala
                20                  25                  30

Thr Gln Arg Ser Ala Asn Glu Asp Lys Ala Ala Asp Leu Gln Arg Glu
            35                  40                  45

Val Glu Arg Asp Gly Gly Arg Phe Arg Phe Val Gly His Phe Ser Glu
        50                  55                  60

Ala Pro Gly Thr Ser Ala Phe Gly Thr Ala Glu Arg Pro Glu Phe Glu
65                  70                  75                  80

Arg Ile Leu Asn Glu Cys Arg Ala Gly Arg Leu Asn Met Ile Ile Val
                85                  90                  95

Tyr Asp Val Ser Arg Phe Ser Arg Leu Lys Val Met Asp Ala Ile Pro
                100                 105                 110

Ile Val Ser Glu Leu Leu Ala Leu Gly Val Thr Ile Val Ser Thr Gln
            115                 120                 125

Glu Gly Val Phe Arg Gln Gly Asn Val Met Asp Leu Ile His Leu Ile
        130                 135                 140

Met Arg Leu Asp Ala Ser His Lys Glu Ser Ser Leu Lys Ser Ala Lys
145                 150                 155                 160

Ile Leu Asp Thr Lys Asn Leu Gln Arg Glu Leu Gly Gly Tyr Val Gly
                165                 170                 175

Gly Lys Ala Pro Tyr Gly Phe Glu Leu Val Ser Glu Thr Lys Glu Ile
                180                 185                 190

Thr Arg Asn Gly Arg Met Val Asn Val Val Ile Asn Lys Leu Ala His
            195                 200                 205
```

```
Ser Thr Thr Pro Leu Thr Gly Pro Phe Glu Phe Glu Pro Asp Val Ile
    210                 215                 220

Arg Trp Trp Arg Glu Ile Lys Thr His Lys His Leu Pro Phe Lys
225                 230                 235                 240

Pro Gly Ser Gln Ala Ala Ile His Pro Gly Ser Ile Thr Gly Leu Cys
                245                 250                 255

Lys Arg Met Asp Ala Asp Ala Val Pro Thr Arg Gly Glu Thr Ile Gly
            260                 265                 270

Lys Lys Thr Ala Ser Ser Ala Trp Asp Pro Ala Thr Val Met Arg Ile
                275                 280                 285

Leu Arg Asp Pro Arg Ile Ala Gly Phe Ala Ala Glu Val Ile Tyr Lys
        290                 295                 300

Lys Lys Pro Asp Gly Thr Pro Thr Thr Lys Ile Glu Gly Tyr Arg Ile
305                 310                 315                 320

Gln Arg Asp Pro Ile Thr Leu Arg Pro Val Glu Leu Asp Cys Gly Pro
                325                 330                 335

Ile Ile Glu Pro Ala Glu Trp Tyr Glu Leu Gln Ala Trp Leu Asp Gly
            340                 345                 350

Arg Gly Arg Gly Lys Gly Leu Ser Arg Gly Gln Ala Ile Leu Ser Ala
        355                 360                 365

Met Asp Lys Leu Tyr Cys Glu Cys Gly Ala Val Met Thr Ser Lys Arg
370                 375                 380

Gly Glu Glu Ser Ile Lys Asp Ser Tyr Arg Cys Arg Arg Lys Val
385                 390                 395                 400

Val Asp Pro Ser Ala Pro Gly Gln His Glu Gly Thr Cys Asn Val Ser
                405                 410                 415

Met Ala Ala Leu Asp Lys Phe Val Ala Glu Arg Ile Phe Asn Lys Ile
            420                 425                 430

Arg His Ala Glu Gly Asp Glu Thr Leu Ala Leu Leu Trp Glu Ala
        435                 440                 445

Ala Arg Arg Phe Gly Lys Leu Thr Glu Ala Pro Glu Lys Ser Gly Glu
450                 455                 460

Arg Ala Asn Leu Val Ala Glu Arg Ala Asp Ala Leu Asn Ala Leu Glu
465                 470                 475                 480

Glu Leu Tyr Glu Asp Arg Ala Ala Gly Ala Tyr Asp Gly Pro Val Gly
                485                 490                 495

Arg Lys His Phe Arg Lys Gln Gln Ala Ala Leu Thr Leu Arg Gln Gln
            500                 505                 510

Gly Ala Glu Glu Arg Leu Ala Glu Leu Glu Ala Ala Glu Ala Pro Lys
        515                 520                 525

Leu Pro Leu Asp Gln Trp Phe Pro Glu Asp Ala Asp Ala Asp Pro Thr
    530                 535                 540

Gly Pro Lys Ser Trp Trp Gly Arg Ala Ser Val Asp Lys Arg Met
545                 550                 555                 560

Phe Val Gly Leu Phe Asp Lys Ile Val Val Thr Lys Ser Thr Thr
                565                 570                 575

Gly Arg Gly Gln Gly Thr Pro Ile Glu Lys Arg Ala Ser Ile Thr Trp
            580                 585                 590

Ala Lys Pro Pro Thr Asp Asp Glu Asp Ala Gln Asp Gly Thr
        595                 600                 605

Gln Asp Val Ala Ala
610
```

<210> SEQ ID NO 23
<211> LENGTH: 613
<212> TYPE: PRT
<213> ORGANISM: Artificial Sequence
<220> FEATURE:
<223> OTHER INFORMATION: Description of Artificial Sequence:altered recombinase 5C1

<400> SEQUENCE: 23

```
Met Thr Gln Gly Val Val Thr Gly Val Asp Thr Tyr Ala Gly Ala Tyr
  1               5                  10                  15

Asp Arg Gln Ser Arg Glu Arg Glu Asn Ser Ser Ala Ala Ser Pro Ala
             20                  25                  30

Thr Gln Arg Ser Ala Asn Glu Asp Lys Ala Ala Asp Leu Gln Arg Glu
         35                  40                  45

Val Glu Arg Asp Gly Gly Arg Phe Arg Phe Val Gly His Phe Ser Glu
     50                  55                  60

Ala Pro Gly Thr Ser Ala Phe Gly Thr Ala Glu Arg Pro Glu Phe Glu
 65                  70                  75                  80

Arg Ile Leu Asn Glu Cys Arg Ala Gly Arg Leu Asn Met Ile Ile Val
                 85                  90                  95

Tyr Asp Val Ser Arg Phe Ser Arg Leu Lys Val Met Asp Ala Ile Pro
            100                 105                 110

Ile Val Ser Glu Leu Leu Ala Leu Gly Val Thr Ile Val Ser Thr Gln
        115                 120                 125

Glu Gly Val Phe Arg Gln Gly Asn Val Met Asp Leu Ile His Leu Ile
    130                 135                 140

Met Arg Leu Asp Ala Ser His Lys Glu Ser Ser Leu Lys Ser Ala Lys
145                 150                 155                 160

Ile Leu Asp Thr Lys Asn Leu Gln Arg Glu Leu Gly Gly Tyr Val Gly
                165                 170                 175

Gly Lys Ala Pro Tyr Gly Phe Glu Leu Val Ser Glu Thr Lys Glu Ile
            180                 185                 190

Thr Arg Asn Gly Arg Met Val Asn Val Val Ile Asn Lys Leu Ala His
        195                 200                 205

Ser Thr Thr Pro Leu Thr Gly Pro Phe Glu Phe Glu Pro Asp Val Ile
    210                 215                 220

Arg Trp Trp Arg Glu Ile Lys Thr His Lys His Leu Pro Phe Lys
225                 230                 235                 240

Pro Gly Ser Gln Ala Thr Ile His Pro Gly Ser Ile Thr Gly Leu Cys
                245                 250                 255

Lys Arg Met Asp Ala Asp Ala Val Pro Thr Arg Gly Glu Thr Ile Gly
            260                 265                 270

Lys Lys Thr Ala Ser Ser Ala Trp Asp Pro Ala Thr Val Met Arg Ile
        275                 280                 285

Leu Arg Asp Pro Arg Ile Ala Gly Phe Ala Ala Glu Val Ile Tyr Lys
    290                 295                 300

Lys Lys Pro Asp Gly Thr Pro Thr Thr Lys Ile Glu Gly Tyr Arg Ile
305                 310                 315                 320

Gln Arg Asp Pro Ile Thr Leu Arg Pro Val Glu Leu Asp Cys Gly Pro
                325                 330                 335

Ile Ile Glu Pro Ala Glu Trp Tyr Glu Leu Gln Ala Trp Leu Asp Gly
            340                 345                 350

Arg Gly Arg Gly Lys Gly Leu Ser Arg Gly Gln Ala Ile Leu Ser Ala
        355                 360                 365
```

```
Met Gly Lys Leu Tyr Cys Glu Cys Gly Ala Val Met Thr Ser Lys Arg
    370                 375                 380
Gly Glu Glu Ser Ile Lys Asp Ser Tyr Arg Cys Arg Arg Arg Lys Val
385                 390                 395                 400
Val Asp Pro Ser Ala Pro Gly Gln His Glu Gly Thr Cys Asn Val Ser
                405                 410                 415
Met Ala Ala Leu Asp Lys Phe Val Ala Glu Arg Ile Phe Asn Lys Ile
            420                 425                 430
Arg His Ala Glu Gly Asp Glu Glu Thr Leu Ala Leu Leu Trp Glu Ala
        435                 440                 445
Ala Arg Arg Phe Gly Lys Leu Thr Glu Ala Pro Glu Lys Ser Gly Glu
    450                 455                 460
Arg Ala Asn Leu Val Ala Glu Arg Ala Asp Ala Leu Asn Ala Leu Glu
465                 470                 475                 480
Glu Leu Tyr Glu Asp Arg Ala Ala Gly Ala Tyr Asp Gly Pro Val Gly
                485                 490                 495
Arg Lys His Phe Arg Lys Gln Gln Ala Ala Leu Thr Leu Arg Gln Gln
            500                 505                 510
Gly Ala Glu Glu Arg Leu Ala Glu Leu Glu Ala Ala Glu Ala Pro Lys
        515                 520                 525
Leu Pro Leu Asp Gln Trp Phe Pro Glu Asp Ala Asp Ala Asp Pro Thr
    530                 535                 540
Gly Pro Lys Ser Trp Trp Gly Arg Ala Ser Val Asp Asp Lys Arg Val
545                 550                 555                 560
Phe Val Gly Leu Phe Val Asp Lys Ile Val Val Thr Lys Ser Thr Thr
                565                 570                 575
Gly Arg Gly Gln Gly Thr Pro Ile Glu Lys Arg Ala Ser Ile Thr Trp
            580                 585                 590
Ala Lys Pro Pro Thr Asp Asp Glu Asp Asp Ala Gln Asp Gly Thr
        595                 600                 605
Glu Asp Val Ala Ala
    610

<210> SEQ ID NO 24
<211> LENGTH: 610
<212> TYPE: PRT
<213> ORGANISM: Artificial Sequence
<220> FEATURE:
<223> OTHER INFORMATION: Description of Artificial Sequence:altered
      recombinase 1C1

<400> SEQUENCE: 24

Met Thr Gln Gly Val Val Thr Gly Val Asp Thr Tyr Ala Gly Ala Tyr
1               5                   10                  15
Asp Arg Gln Ser Arg Glu Arg Glu Asn Ser Ser Ala Ala Ser Pro Ala
                20                  25                  30
Thr Gln Arg Ser Ala Asn Glu Asp Lys Ala Ala Asp Leu Gln Arg Glu
            35                  40                  45
Val Glu Arg Asp Gly Gly Arg Phe Arg Phe Val Gly His Phe Ser Glu
        50                  55                  60
Ala Pro Gly Thr Ser Ala Phe Gly Thr Ala Glu Arg Pro Glu Phe Glu
65                  70                  75                  80
Arg Ile Leu Asn Glu Cys Arg Ala Gly Arg Leu Asn Met Ile Ile Val
                85                  90                  95
Tyr Asp Val Ser Arg Phe Ser Arg Leu Lys Val Met Asp Ala Ile Pro
            100                 105                 110
```

-continued

Ile Val Ser Glu Leu Leu Ala Leu Gly Val Thr Ile Val Ser Thr Gln
        115                 120                 125

Glu Gly Val Phe Arg Gln Gly Asn Val Met Asp Leu Ile His Leu Ile
    130                 135                 140

Met Arg Leu Asp Ala Ser His Lys Glu Ser Ser Leu Lys Ser Ala Lys
145                 150                 155                 160

Ile Leu Asp Thr Lys Asn Leu Gln Arg Glu Leu Gly Gly Tyr Val Gly
                165                 170                 175

Gly Lys Ala Pro Tyr Gly Phe Glu Leu Val Ser Glu Thr Lys Glu Ile
            180                 185                 190

Thr Arg Asn Gly Arg Met Val Asn Val Ile Asn Lys Leu Ala His
        195                 200                 205

Ser Thr Thr Pro Leu Thr Gly Pro Phe Glu Phe Pro Asp Val Ile
    210                 215                 220

Arg Trp Trp Arg Glu Ile Lys Thr His Lys His Leu Pro Phe Lys
225                 230                 235                 240

Pro Gly Ser Gln Ala Ala Ile His Pro Gly Ser Ile Thr Gly Leu Cys
                245                 250                 255

Lys Arg Met Asp Ala Asp Ala Val Pro Thr Arg Gly Glu Thr Ile Gly
            260                 265                 270

Lys Lys Thr Ala Ser Ser Ala Trp Asp Pro Ala Thr Val Met Arg Ile
        275                 280                 285

Leu Arg Asp Pro Arg Ile Ala Gly Phe Ala Ala Glu Val Ile Tyr Lys
    290                 295                 300

Lys Lys Pro Asp Gly Thr Pro Thr Thr Lys Ile Glu Gly Tyr Arg Ile
305                 310                 315                 320

Gln Arg Asp Pro Ile Thr Leu Arg Pro Val Glu Leu Asp Cys Gly Pro
                325                 330                 335

Ile Ile Glu Pro Ala Glu Trp Tyr Glu Leu Gln Ala Trp Leu Asp Gly
            340                 345                 350

Arg Gly Arg Gly Lys Gly Leu Ser Arg Gly Gln Ala Ile Leu Ser Ala
        355                 360                 365

Met Asp Lys Leu Tyr Cys Glu Cys Gly Ala Ile Met Thr Ser Lys Arg
    370                 375                 380

Gly Glu Glu Ser Ile Lys Asp Ser Tyr Arg Cys Arg Arg Lys Val
385                 390                 395                 400

Val Asp Pro Ser Ala Pro Gly Gln His Glu Gly Thr Cys Asn Val Ser
                405                 410                 415

Met Ala Ala Leu Asp Lys Phe Val Ala Glu Arg Ile Phe Asn Lys Ile
            420                 425                 430

Arg His Ala Glu Gly Asp Glu Glu Thr Leu Ala Leu Leu Trp Glu Ala
        435                 440                 445

Ala Arg Arg Phe Gly Lys Leu Thr Glu Ala Pro Glu Lys Ser Gly Glu
    450                 455                 460

Arg Ala Asn Leu Val Ala Glu Arg Ala Asp Ala Leu Asn Ala Leu Glu
465                 470                 475                 480

Glu Leu Tyr Glu Asp Arg Ala Ala Gly Ala Tyr Asp Gly Pro Val Gly
                485                 490                 495

Arg Lys His Phe Arg Lys Gln Gln Ala Ala Leu Thr Leu Arg Gln Gln
            500                 505                 510

Gly Ala Glu Glu Arg Leu Ala Glu Leu Glu Ala Ala Glu Ala Pro Lys
        515                 520                 525

-continued

```
Leu Pro Leu Asp Gln Trp Phe Pro Glu Asp Ala Asp Ala Asp Pro Thr
    530                 535                 540
Gly Pro Lys Ser Trp Trp Gly Arg Ala Ser Val Asp Lys Arg Val
545                 550                 555                 560
Phe Val Gly Leu Phe Val Asp Lys Ile Val Val Thr Lys Ser Thr Thr
                    565                 570                 575
Gly Arg Gly Gln Gly Thr Pro Ile Glu Lys Arg Ala Ser Ile Thr Trp
                580                 585                 590
Ala Lys Pro Pro Thr Asp Asp Glu Asp Asp Ala Arg Thr Ala Arg
            595                 600                 605
Lys Thr
    610
```

<210> SEQ ID NO 25
<211> LENGTH: 613
<212> TYPE: PRT
<213> ORGANISM: Artificial Sequence
<220> FEATURE:
<223> OTHER INFORMATION: Description of Artificial Sequence:consensus
      sequence
<220> FEATURE:
<221> NAME/KEY: MUTAGEN
<222> LOCATION: (246)
<223> OTHER INFORMATION: where XAA indicates no consensus amino acid at
      this position in Figs 3A and 3B
<220> FEATURE:
<221> NAME/KEY: MUTAGEN
<222> LOCATION: (370)
<223> OTHER INFORMATION: where XAA indicates no consensus amino acid at
      this position in Figs 3A and 3B
<220> FEATURE:
<221> NAME/KEY: MUTAGEN
<222> LOCATION: (379)
<223> OTHER INFORMATION: where XAA indicates no consensus amino acid at
      this position in Figs 3A and 3B
<220> FEATURE:
<221> NAME/KEY: MUTAGEN
<222> LOCATION: (560)
<223> OTHER INFORMATION: where XAA indicates no consensus amino acid at
      this position in Figs 3A and 3B
<220> FEATURE:
<221> NAME/KEY: MUTAGEN
<222> LOCATION: (605)..(613)
<223> OTHER INFORMATION: where XAA indicates no consensus amino acid at
      this position in Figs 3A and 3B

<400> SEQUENCE: 25

```
Met Thr Gln Gly Val Val Thr Gly Val Asp Thr Tyr Ala Gly Ala Tyr
 1               5                  10                  15
Asp Arg Gln Ser Arg Glu Arg Glu Asn Ser Ser Ala Ala Ser Pro Ala
                20                  25                  30
Thr Gln Arg Ser Ala Asn Glu Asp Lys Ala Ala Asp Leu Gln Arg Glu
            35                  40                  45
Val Glu Arg Asp Gly Gly Arg Phe Arg Phe Val Gly His Phe Ser Glu
        50                  55                  60
Ala Pro Gly Thr Ser Ala Phe Gly Thr Ala Glu Arg Pro Glu Phe Glu
65                  70                  75                  80
Arg Ile Leu Asn Glu Cys Arg Ala Gly Arg Leu Asn Met Ile Ile Val
                85                  90                  95
Tyr Asp Val Ser Arg Phe Ser Arg Leu Lys Val Met Asp Ala Ile Pro
                100                 105                 110
Ile Val Ser Glu Leu Leu Ala Leu Gly Val Thr Ile Val Ser Thr Gln
            115                 120                 125
Glu Gly Val Phe Arg Gln Gly Asn Val Met Asp Leu Ile His Leu Ile
```

-continued

```
            130                 135                 140
Met Arg Leu Asp Ala Ser His Lys Glu Ser Ser Leu Lys Ser Ala Lys
145                 150                 155                 160

Ile Leu Asp Thr Lys Asn Leu Gln Arg Glu Leu Gly Gly Tyr Val Gly
                165                 170                 175

Gly Lys Ala Pro Tyr Gly Phe Glu Leu Val Ser Glu Thr Lys Glu Ile
                180                 185                 190

Thr Arg Asn Gly Arg Met Val Asn Val Ile Asn Lys Leu Ala His
                195                 200                 205

Ser Thr Thr Pro Leu Thr Gly Pro Phe Glu Phe Glu Pro Asp Val Ile
210                 215                 220

Arg Trp Trp Arg Glu Ile Lys Thr His Lys His Leu Pro Phe Lys
225                 230                 235                 240

Pro Gly Ser Gln Ala Xaa Ile His Pro Gly Ser Ile Thr Gly Leu Cys
                245                 250                 255

Lys Arg Met Asp Ala Asp Ala Val Pro Thr Arg Gly Glu Thr Ile Gly
                260                 265                 270

Lys Lys Thr Ala Ser Ser Ala Trp Asp Pro Ala Thr Val Met Arg Ile
            275                 280                 285

Leu Arg Asp Pro Arg Ile Ala Gly Phe Ala Ala Glu Val Ile Tyr Lys
            290                 295                 300

Lys Lys Pro Asp Gly Thr Pro Thr Thr Lys Ile Glu Gly Tyr Arg Ile
305                 310                 315                 320

Gln Arg Asp Pro Ile Thr Leu Arg Pro Val Glu Leu Asp Cys Gly Pro
                325                 330                 335

Ile Ile Glu Pro Ala Glu Trp Tyr Glu Leu Gln Ala Trp Leu Asp Gly
                340                 345                 350

Arg Gly Arg Gly Lys Gly Leu Ser Arg Gly Gln Ala Ile Leu Ser Ala
            355                 360                 365

Met Xaa Lys Leu Tyr Cys Glu Cys Gly Ala Xaa Met Thr Ser Lys Arg
            370                 375                 380

Gly Glu Glu Ser Ile Lys Asp Ser Tyr Arg Cys Arg Arg Lys Val
385                 390                 395                 400

Val Asp Pro Ser Ala Pro Gly Gln His Glu Gly Thr Cys Asn Val Ser
                405                 410                 415

Met Ala Ala Leu Asp Lys Phe Val Ala Glu Arg Ile Phe Asn Lys Ile
                420                 425                 430

Arg His Ala Glu Gly Asp Glu Glu Thr Leu Ala Leu Leu Trp Glu Ala
            435                 440                 445

Ala Arg Arg Phe Gly Lys Leu Thr Glu Ala Pro Glu Lys Ser Gly Glu
450                 455                 460

Arg Ala Asn Leu Val Ala Glu Arg Ala Asp Ala Leu Asn Ala Leu Glu
465                 470                 475                 480

Glu Leu Tyr Glu Asp Arg Ala Ala Gly Ala Tyr Asp Gly Pro Val Gly
                485                 490                 495

Arg Lys His Phe Arg Lys Gln Gln Ala Ala Leu Thr Leu Arg Gln Gln
                500                 505                 510

Gly Ala Glu Glu Arg Leu Ala Glu Leu Glu Ala Glu Ala Pro Lys
            515                 520                 525

Leu Pro Leu Asp Gln Trp Phe Pro Glu Asp Ala Asp Ala Asp Pro Thr
530                 535                 540

Gly Pro Lys Ser Trp Trp Gly Arg Ala Ser Val Asp Asp Lys Arg Xaa
545                 550                 555                 560
```

```
Phe Val Gly Leu Phe Val Asp Lys Ile Val Val Thr Lys Ser Thr Thr
            565                 570                 575

Gly Arg Gly Gln Gly Thr Pro Ile Glu Lys Arg Ala Ser Ile Thr Trp
            580                 585                 590

Ala Lys Pro Pro Thr Asp Asp Glu Asp Asp Ala Xaa Xaa Xaa Xaa
            595                 600                 605

Xaa Xaa Xaa Xaa Xaa
        610

<210> SEQ ID NO 26
<211> LENGTH: 1842
<212> TYPE: DNA
<213> ORGANISM: Artificial Sequence
<220> FEATURE:
<223> OTHER INFORMATION: Description of Artificial Sequence:altered
      recombinase 7C1

<400> SEQUENCE: 26
atgacacaag gggttgtgac cggggtggac acgtacgcgg gtgcttacga ccgtcagtcg      60
cgcgagcgcg aaaattcgag cgcagcaagc cagcgacaca gcgtagcgc caacgaagac     120
aaggcggccg accttcagcg cgaagtcgag cgcgacgggg gccggttcag gttcgtcggg    180
catttcagcg aagcgccggg cacgtcggcg ttcgggacgg cggagcgccc ggagttcgaa    240
cgcatcctga cgaatgccg cgccgggcgg ctcaacatga tcattgtcta tgacgtgtcg     300
cgcttctcgc gcctgaaggt catggacgcg attccgattg tctcggaatt gctcgccctg    360
ggcgtgacga ttgtttccac tcaggaaggc gtcttccggc agggaaacgt catggacctg    420
attcacctga ttatgcggct cgacgcgtcg cacaaagaat cttcgctgaa gtcggcgaag    480
attctcgaca cgaagaacct tcagcgcgaa ttgggcgggt acgtcggcgg aaggcgcct    540
tacggcttcg agcttgtttc ggagacgaag gagatcacgc gcaacggccg aatggtcaat    600
gtcgtcatca acaagcttgc gcactcgacc actcccctta ccggacccctt cgagttcgag    660
cccgacgtaa tccggtggtg gtggcgtgag atcaagacgc acaaacacct tcccttcaag    720
ccgggcagtc aagccgccat tcacccgggc agcatcacgg gctttgtaa gcgcatggac    780
gctgacgccg tgccgacccg gggcgagacg attgggaaga agaccgcttc aagcgcctgg    840
gacccggcaa ccgttatgcg aatccttcgg gacccgcgta tcgcgggctt cgccgctgag    900
gtgatctaca agaagaagcc ggacggcacg ccgaccacga agattgaggg ttaccgcatt    960
cagcgcgacc cgatcacgct ccggccggtc gagcttgatt gcggaccgat catcgagccc   1020
gctgagtggt atgagcttca ggcgtggttg gacggcaggg ggcgcggcaa ggggctttcc   1080
cggggggcaag ccattctgtc cgccatggac aagctgtact gcgagtgtgg cgccgtcatg   1140
acttcgaagc gcggggaaga atcgatcaag gactcttacc gctgccgtcg ccggaaggtg   1200
gtcgacccgt ccgcacctgg gcagcacgaa ggcacgtgca acgtcagcat ggcggcactc   1260
gacaagttcg ttgcggaacg catcttcaac aagatcaggc acgccgaagg cgacgaagag   1320
acgttggcgc ttctgtggga agccgcccga cgcttcggca agctcactga ggcgcctgag   1380
aagagcggcg aacgggcgaa ccttgttgcg gagcgcgccg acgccctgaa cgcccttgaa   1440
gagctgtacg aagaccgcgc ggcaggcgcg tacgacggac ccgttggcag gaagcacttc   1500
cggaagcaac aggcagcgct gacgctccgg cagcaagggg cggaagagcg gcttgccgaa   1560
cttgaagccg ccgaagcccc gaagcttccc cttgaccaat ggttcccga agacgccgac   1620
gctgacccga ccggccctaa gtcgtggtgg gggcgcgcgt cagtagacga caagcgcatg   1680
```

```
ttcgtcgggc tcttcgtaga caagatcgtt gtcacgaagt cgactacggg caggggggcag    1740 ggaacgccca tcgagaagcg cgcttcgatc acgtgggcga agccgccgac cgacgacgac    1800
gaagacgacg cccaggacgg cacgcaagac gtagcggcgt ag                        1842

<210> SEQ ID NO 27
<211> LENGTH: 1839
<212> TYPE: DNA
<213> ORGANISM: Artificial Sequence
<220> FEATURE:
<223> OTHER INFORMATION: Description of Artificial Sequence:altered
      recombinase 5C1

<400> SEQUENCE: 27
atgacacaag gggttgtgac cggggtggac acgtacgcgg gtgcttacga ccgtcagtcg      60
cgcgagcgcg aaaattcgag cgcagcaagc ccagcgacac agcgtagcgc caacgaagac    120
aaggcggccg accttcagcg cgaagtcgag cgcgacgggg ccggttcag attcgtcggg     180 catttcagcg aagcgccggg cacgtcggcg ttcgggacgg cggagcgccc ggagttcgaa    240
cgcatcctga cgaatgccg cgccgggcgg ctcaacatga tcattgtcta tgacgtgtcg     300
cgcttctcgc gcctgaaggt catggacgcg attccgattg tctcggaatt gctcgccctg    360
ggcgtgacga ttgttccac tcaggaaggc gtcttccggc agggaaacgt catggacctg    420
attcacctga ttatgcggct cgacgcgtcg cacaaagaat cttcgctgaa gtcggcgaag    480
attctcgaca cgaagaacct tcagcgcgaa ttgggcgggt acgtcggcgg gaaggcgcct    540
tacggcttcg agcttgtttc ggagacgaag gagatcacgc gcaacggccg aatggtcaat    600
gtcgtcatca acaagcttgc gcactcgacc actccccta ccggaccctt cgagttcgag    660
cccgacgtaa tccggtggtg gtggcgtgag atcaagacgc acaaacacct tcccttcaag    720
ccgggcagtc aagccaccat tcacccgggc agcatcacgg ggctttgtaa gcgcatggac    780
gctgacgccg tgccgacccg gggcgagacg attgggaaga gaccgcttc aagcgcctgg    840 gacccggcaa ccgttatgcg aatccttcg gaccgcgta ttgcgggctt cgccgctgag    900
gtgatctaca agaagaagcc ggacggcacg ccgaccacga agattgaggg ttaccgcatt    960
cagcgcgacc cgatcacgct ccggccggtc gagcttgatt gcggaccgat catcgagccc   1020
gctgagtggt atgagcttca ggcgtggttg gacggcaggg ggcgcggcaa ggggctttcc   1080
cgggggcaag ccattctgtc cgccatgggc aagctgtact gcgagtgtgg cgccgtcatg   1140
acttcgaagc gcggggaaga atcgatcaag gactcttacc gctgccgtcg ccggaaggtg   1200
gtcgacccgt ccgcacctgg gcagcacgaa ggcacgtgca acgtcagcat ggcggcactc   1260
gacaagttcg ttgcggaacg catcttcaac aagatcaggc acgccgaagg cgacgaagag   1320
acgttggcgc ttctgtggga agccgcccga cgcttcggca agctcactga ggcgcctgag   1380
aagagcggcc aacgggcgaa ccttgttgcg gagcgcgccg acgccctgaa cgcccttgaa   1440
gagctgtacg aagaccgcgc ggcaggcgcg tacgacggac ccgttggcag gaagcacttc   1500
cggaagcaac aggcagcgct gacgctccgg cagcaagggg cggaagagcg gcttgccgaa   1560
cttgaagccg ccgaagcccc gaagcttccc cttgaccaat ggttccccga agacgccgac   1620 gctgaccccga ccgccctaa gtcgtggtgg gggcgcgcgt cagtagacga caagcgcgtg   1680
ttcgtcgggc tcttcgtaga caagatcgtt gtcacgaagt cgactacggg caggggggcag   1740 ggaacgccca tcgagaagcg cgcttcgatc acgtgggcga agccgccaac cgacgacgac   1800
gaagacgacg cccaggacgg cacggaagac gtagcggcg                           1839
```

-continued

<210> SEQ ID NO 28
<211> LENGTH: 1833
<212> TYPE: DNA
<213> ORGANISM: Artificial Sequence
<220> FEATURE:
<223> OTHER INFORMATION: Description of Artificial Sequence:altered
      recombinase 1C1

<400> SEQUENCE: 28

| | | |
|---|---|---|
| atgacacaag gggttgtgac cggggtggac acgtacgcgg gtgcttacga ccgtcagtcg | 60 |
| cgcgagcgcg aaaattcgag cgcagcaagc cagcgacac agcgtagcgc caacgaagac | 120 |
| aaggcggccg accttcagcg cgaagtcgag cgcgacgggg gccggttcag gttcgtcggg | 180 |
| catttcagcg aagcgccggg cacgtcggcg ttcgggacgc cggaacgccc ggagttcgaa | 240 |
| cgcatcctga acgaatgccg cgccgggcgg ctcaacatga tcattgtcta tgacgtgtcg | 300 |
| cgcttctcgc gcctgaaggt catggacgcg attccgattg tctcggaatt gctcgccctg | 360 |
| ggcgtgacga ttgtttccac tcaggaaggc gtcttccggc agggaaacgt catggacctg | 420 |
| attcacctga ttatgcggct cgacgcgtcg cacaaagaat cttcgctgaa gtcggcgaag | 480 |
| attctcgaca cgaagaacct tcagcgcgaa ctgggcgggt acgtcggcgg aaggcgcct | 540 |
| tacggcttcg agcttgtttc ggagacgaag gagatcacgc gcaacggccg aatggtcaat | 600 |
| gtcgtcatca acaagcttgc gcactcgacc actccccttta ccggacccct tcgagttcgag | 660 |
| cccgacgtaa tccggtggtg gtggcgtgag atcaagacgc acaaacacct tcccttcaag | 720 |
| ccgggcagtc aagccgccat tcacccgggc agcatcacgg ggctttgtaa gcgcatggac | 780 |
| gctgacgccg tgccgacccg gggcgagacg attgggaaga agaccgcttc aagcgcctgg | 840 |
| gacccggcaa ccgttatgcg aatccttcgg gacccgcgta ttgcgggctt cgccgctgag | 900 |
| gtgatctaca agaagaagcc ggacggcacg ccgaccacga agattgaggg ttaccgcatt | 960 |
| cagcgcgacc cgatcacgct ccggccggtc gagcttgatt gcggaccgat catcgagccc | 1020 |
| gctgagtggt atgagcttca ggcgtggttg gacggcaggg ggcgcggcaa ggggctttcc | 1080 |
| cggggggcaag ccattctgtc cgccatggac aagctgtact gcgagtgtgg cgccatcatg | 1140 |
| acttcgaagc gcggggaaga atcgatcaag gactcttacc gctgccgtcg ccggaaggtg | 1200 |
| gtcgacccgt ccgcacctgg gcagcacgaa ggcacgtgca acgtcagcat ggcggcactc | 1260 |
| gacaagttcg ttgcggaacg catcttcaac aagatcaggc acgccgaagg cgacgaagag | 1320 |
| acgttggcgc ttctgtggga agccgcccga cgcttcggca agctcactga ggcgcctgag | 1380 |
| aagagcggcg aacgggcgaa ccttgttgcg gagcgcgccg acgccctgaa cgcccttgaa | 1440 |
| gagctgtacg aagaccgcgc ggcaggcgcg tacgacggac ccgttggcag gaagcacttc | 1500 |
| cggaagcagc aggcagcgct gacgctccgg cagcaagggg cggaagagcg gcttgccgaa | 1560 |
| cttgaagccg ccgaagcccc gaagcttccc cttgaccaat ggttccccga agacgccgac | 1620 |
| gctgacccga ccggccctaa gtcgtggtgg gggcgcgcgt cagtagacga caagcgcgtg | 1680 |
| ttcgtcgggc tcttcgtaga caagattgtt gtcacgaagt cgactacggg caggggggcag | 1740 |
| ggaacgccca tcgagaagcg cgcttcgatc acgtgggcga agccgccgac cgacgacgac | 1800 |
| gaagacgacg ccaggacggc acggaagacg tag | 1833 |

<210> SEQ ID NO 29
<211> LENGTH: 218
<212> TYPE: DNA
<213> ORGANISM: Artificial Sequence
<220> FEATURE:
<223> OTHER INFORMATION: Description of Artificial Sequence:full length
      phiC31 attP

<400> SEQUENCE: 29
ccggtactga cggacacacc gaagccccgg cggcaaccct cagcggatgc cccggggctt    60
cacgttttcc caggtcagaa gcggttttcg ggagtagtgc cccaactggg gtaacctttg   120
agttctctca gttgggggcg tagggtcgcc gacatgacac aagggggttgt gaccggggtg  180 gacacgtacg cgggtgctta cgaccgtcag tcgcggcc                           218

<210> SEQ ID NO 30
<211> LENGTH: 279
<212> TYPE: DNA
<213> ORGANISM: Artificial Sequence
<220> FEATURE:
<223> OTHER INFORMATION: Description of Artificial Sequence:full length
      phiC31 attB

<400> SEQUENCE: 30
cgatgtaggt cacggtctcg aagccgcggt gcgggtgcca ggcgtgccc ttgggctccc     60 cgggcgcgta ctccacctca cccatctggt ccatcatgat gaacgggtcg aggtggcggt   120
agttgatccc ggcgaacgcg cggcgcaccg ggaagccctc gccctcgaaa ccgctgggcg   180
cggtggtcac ggtgagcacg ggacgtgcga cggcgtcggc gggtgcggat acgcggggca   240
gcgtcagcgg gttctcgacg gtcacggcgg gcatgtcga                          279

<210> SEQ ID NO 31
<211> LENGTH: 295
<212> TYPE: DNA
<213> ORGANISM: Artificial Sequence
<220> FEATURE:
<223> OTHER INFORMATION: Description of Artificial Sequence:R4
      recombinase attB

<400> SEQUENCE: 31
cgtggggacg ccgtacaggg acgtgcacct ctcccgctgc accgcctcca gcgtcgccgc    60
cggctcgaag gacggggccg ggatgacgat gcaggcggcg tgggaggtgg cgcccaagtt   120
gcccatgacc atgccgaagc agtggtagaa gggcaccggc agacacaccc ggtcctgctc   180
cgtgtagccg accgtgcggc ccacccagta gccgttgttg aggatgttgt ggtgggagag   240
cgtggcgccc ttggggaagc cggtggtgcc ggaggtgtac tggatgttga ccggg        295

<210> SEQ ID NO 32
<211> LENGTH: 64
<212> TYPE: DNA
<213> ORGANISM: Artificial Sequence
<220> FEATURE:
<223> OTHER INFORMATION: Description of Artificial Sequence:R4
      recombinase attP

<400> SEQUENCE: 32
gcatgttccc caaagcgata ccacttgaag cagtggtact gcttgtgggt acactctgcg    60
ggtg                                                                64

<210> SEQ ID NO 33
<211> LENGTH: 59
<212> TYPE: DNA
<213> ORGANISM: Artificial Sequence
<220> FEATURE:
<223> OTHER INFORMATION: Description of Artificial Sequence:a wild-type
      phiC31 attP

```
<400> SEQUENCE: 33
ggagtagtgc cccaactggg gtaacctttg agttctctca gttgggggcg tagggtcgc        59

<210> SEQ ID NO 34
<211> LENGTH: 475
<212> TYPE: DNA
<213> ORGANISM: Artificial Sequence
<220> FEATURE:
<223> OTHER INFORMATION: Description of Artificial Sequence:psiA site

<400> SEQUENCE: 34
atttgtagaa ctattatggg acttaaaggg gatatgggag gccacagttg agatgccttc        60
caatcagagg cttggtgaga ttccaagagg tggtttcaaa tacagcaata agtacttggg       120 tttccttgg tgtccccatg gagatttaa gccatgacgc aatgtttaaa tcagagtggt        180
atttttatga cttaagcggg taaatatgca attggaaaat attcagggaa gggtgatttg       240
gtccagaaga gtgggggcat ccagagtaca gtgggtgaaa tggatcggac tttttggaag       300
agagccttgt gctggacagg atggtccagt attgtcaaca caagtttctc atgcttcact       360
ctccttccta gcaacaggaa gacggaaatg aggccatgca aaaataaaag accctgaaag       420
actccagaca atacctgatc caccctacca ttcaccctgt atagccagaa gactt            475
```

ALTERED RECOMBINASES FOR GENOME MODIFICATION

CROSS-REFERENCE TO RELATED APPLICATIONS

This application is related to U.S. Provisional Patent Application Ser. No. 60/183,759, filed 18 Feb. 2000, from which priority is claimed under 35 USC §119(e) (1), and which application is incorporated herein by reference in its entirety.

This invention was made with support under NIH Grant R01 DK55569 and R01 DK58187 from the National Institutes of Health, U.S. Department of Health and Human Services. Accordingly, the United States Government may have certain rights in the invention.

TECHNICAL FIELD OF THE INVENTION

The present invention relates to the field of biotechnology, and more specifically to the field of genomic modification. Disclosed herein are altered recombinases, including compositions thereof, expression vectors, and methods of use thereof, for the generation of transgenic cells, tissues, plants, and animals. The compositions, vectors, and methods of the present invention are also useful in gene therapy techniques.

BACKGROUND OF THE INVENTION

The current inability to perform efficient, site-specific integration of incoming DNA into the chromosomes of higher organisms is holding up advances in basic and applied biology. Recently strategies for chromosomal integration that take advantage of the high efficiency and tight sequence specificity of recombinase enzymes isolated from microorganisms have been described. In particular, a class of phage integrases that includes the φC31 integrase (Kuhstoss, S., and Rao, R. N., J. Mol. Biol. 222, 897–908 (1991); Rausch, H., and Lehmann, M., Nucleic Acids Research 19, 5187–5189 (1991)) have been shown to function in mammalian cells (Groth, A. C., et al., Proc. Natl. Acad. Sci. USA 97, 5995–6000 (2000)).

Such site-specific recombinase enzymes have long DNA recognition sites that are typically not present even in the large genomes of mammalian cells. However, it has been recently demonstrated that recombinase pseudo sites, i.e. sites with a significant degree of identity to the wild-type binding site for the recombinase, are present in these genomes (Thyagarajan, B., et al., Gene 244, 47–54 (2000)).

The present disclosure teaches methods to alter the specificity of recombinases to provide altered recombinases that can be used more effectively in genetic engineering of the chromosomes of higher cells.

SUMMARY OF THE INVENTION

The present invention relates to the identification, isolation, cloning, expression, purification, and methods of use of altered recombinases. In one aspect, the present invention is directed to a method of site-specifically integrating a polynucleotide sequence of interest in a genome of a target cell using an altered recombinase of the present invention.

In one embodiment, the present invention is directed to a method for identifying an altered recombinase. In the method a population of cells is typically provided wherein cells of the population comprise a first plasmid (e.g., a resident plasmid). The first plasmid may comprise a transcriptional promoter region adjacent a first recombination site adjacent a transcription terminator adjacent a second recombination site adjacent a coding sequence of interest. The order of these components is promoter-first recombination site-transcription terminator-second recombination site-coding sequence of interest, wherein said first and second recombination sites act as substrates for a first recombinase and read-through transcription of the coding sequence of interest is minimized or essentially eliminated. The promoter is functional in the cell and an operable linkage of promoter and coding sequence of interest results from a recombination event between the two recombination sites (i.e., the transcription terminator is removed).

The population of cells is then transformed with a group (or population) of second plasmids (e.g., cloning plasmids). The group of plasmids comprises at least one second plasmid comprising a coding sequence for an altered recombinase operable linked to a promoter functional in the cell. Typically the group of plasmids represents a shuffled library of recombinases or mutagenized recombinases. Methods of generating such recombinase variants are described herein. The nucleic acid coding sequence for the altered recombinase typically differs from the coding sequence of the first recombinase (or parent recombinases) by at least one base pair, where that difference typically gives rise to at least one amino acid differences between the polypeptide coding sequences of the altered recombinase and the parent recombinase.

The cells are maintained under conditions that allow recombination to occur between the first and second recombination sites, wherein the recombination event is mediated by the altered recombinase. The population of transformed cells is then screened (or a genetic selection is applied) to identify a product encoded by the coding sequence of interest. Such a product may include, but is not limited to, a product identifiable by screening or selection, such as an RNA product or, ultimately, a polypeptide product. Cells producing the product encoded by the sequence of interest are then isolated and coding sequences of the altered recombinase, encoded by these cells, are isolated and identified.

In a preferred embodiment, the altered recombinase provides an improved recombination frequency between the first and second recombination sites relative to the recombination frequency between the first and second recombination sites mediated by the first recombinase. Identification of variants having reduced or similar recombination frequencies is also possible using the methods of the present invention.

The first or parent recombinase may be, for example, a wild-type phage recombinase such as φC31, TP901-1, and R4. Other recombinases may be used in the method of the present invention as the first recombinase, including altered recombinases identified by previous cycles of screening using the methods of the present invention. Further, altered recombinases may be obtained using more than one "first" recombinase (e.g., in a family shuffling method).

The recombination sites used as substrates in the method of the present invention include, but are not limited to, wild-type attB, wild-type attP, pseudo-attb and pseudo-attP. Typically, at least one of the recombination sites provide a substrate for the first recombinase. Pseudo-sites may be identified, using methods described herein, in the genome of essentially any target cell, including, but not limited to, human and rodent cells.

The method of identifying an altered recombinase can be carried out in a number of cell types as described herein. In a preferred embodiment the method is carried out in bacterial cells.

The coding sequence of interest can encode a product that can be identified by a screen or selection, including, but not limited to, polypeptide products such as beta-galactosidase. Other reporter markers are described herein, as well as selectable markers.

In another aspect the present invention relates to an altered recombinase produced by the methods of the present invention. Typically the altered recombinase comprises a polypeptide wherein at least one amino acid is different from a wild-type sequence of the first recombinase, wherein the altered recombinase has improved recombination efficiency towards wild-type or pseudo att site sequences relative to the first recombinase. As discussed above, altered recombinases identified by the methods of the present invention may have increased, decreased, or similar recombination efficiencies related to the parent recombinases. Exemplary altered recombinases identified by the methods of the present invention include SEQ ID NO:22, SEQ ID NO:23, and SEQ ID NO:24. The present invention also includes nucleic acid sequences encoding the polypeptide sequences of the altered recombinases.

In yet another aspect, the present invention is directed to a method of site-specifically integrating a polynucleotide sequence of interest in a genome of a cell. The method comprises introducing (i) a circular targeting construct, comprising a first recombination site and the polynucleotide sequence of interest, and (ii) an altered recombinase into the cell, wherein the genome of the cell comprises a second recombination site native to the genome and recombination between the first and second recombination sites is facilitated by the site-specific recombinase. The cell is maintained under conditions that allow recombination between the first and second recombination sites and the recombination is mediated by the site-specific recombinase. The result of the recombination is site-specific integration of the polynucleotide sequence of interest in the genome of the cell. In a preferred embodiment, the cell is a eucaryotic cell.

The altered recombinase may be introduced into the cell before, concurrently with, or after introducing the circular targeting construct. The altered recombinase may be introduced, for example, as a polypeptide, or a nucleic acid (such as RNA or DNA) encoding the altered recombinase. Further, the circular targeting construct may comprise other useful components, such as a bacterial origin of replication and/or a selectable marker.

These and other embodiments of the present invention will readily occur to those of ordinary skill in the art in view of the disclosure herein.

BRIEF DESCRIPTION OF THE FIGURES

FIG. 1A illustrates an exemplary "Resident Plasmid" which is established in *E. coli* and bears a lacZ gene separated from its promoter by a stuffer region containing transcriptional termination signals. The stuffer is flanked by two att test sites, i.e., the att sequences between which recombination is to be directed. For example, the human psi-A pseudo attP site and the wild-type attB site. After recombination, lacZ is transcribed, resulting in blue color on X-gal indicator plates. FIG. 1B illustrates an exemplary "Cloning Plasmid" which carries a shuffled library of integrase genes. It is transformed into the recipient strain carrying the Resident Plasmid. After a period of growth on plates at 30° C., the temperature is raised to 37° C., which inactivates the temperature sensitive lacI lac repressor gene located on the Resident Plasmid. The integrase gene on the cloning plasmid, which is transcribed under the control of the lac promoter, is then expressed. Mutant integrases that increase recombination between the att test sites on the Resident Plasmid will give rise to blue colonies. The desired mutant integrase can be recovered from these colonies by purifying the Cloning Plasmid from them.

FIGS. 3A and 3B illustrates the amino acid changes found in three altered integrases detected by increased blueness of colonies on Xgal plates in the assay using the plasmids depicted in FIGS. 1A and 1B and described in Example 1. These mutant integrases, called 1C1, 5C1, and 7C1, were obtained after one round of DNA shuffling. In FIGS. 3A and 3B, the protein sequence for altered recombinase 7C1 (SEQ ID NO:22), wild-type recombinase φC31 (SEQ ID NO:21), altered recombinase 5C1 (SEQ ID NO:23), and altered recombinase 1C1 (SEQ ID NO:24), are presented relative to a consensus sequence (SEQ ID NO:25). The asterisks at the ends of the sequences in FIGS. 3A and 3B represent stop codons.

FIG. 4 presents the DNA sequence of the wild-type φC31 recombinase (SEQ ID NO:20).

FIG. 5 (SEQ ID NO:22) presents the peptide sequence of altered recombinase 7C1.

FIG. 6 (SEQ ID NO:26) presents the DNA sequence of altered recombinase 7C1.

FIG. 7 (SEQ ID NO:23) presents the peptide sequence of altered recombinase 5C1.

FIG. 8 (SEQ ID NO:27) presents DNA sequence of altered recombinase 5C1.

FIG. 9 (SEQ ID NO:24) presents the peptide sequence of recombinase 1C1.

FIG. 10 (SEQ ID NO:28) presents the DNA sequence of altered recombinase 1C1.

FIGS. 11A and 11B present the DNA sequences of the full length φC31 attP (SEQ ID NO:29) and attB (SEQ ID NO:30) sites, respectively. FIG. 11C presents a 59 bp wild-type φC31 attP site (SEQ ID NO:33). In the figures the TTG core is indicated in upper case.

FIGS. 12A and 12B present, respectively, attB (SEQ ID NO:31) and attP (SEQ ID NO:32) sequences for the R4 recombinase.

FIG. 13 (SEQ ID NO:34) shows approximately 475 bp of DNA sequence from human chromosome 8 that encompasses the φC31 integrase pseudo-attp site ψA. The core TTG sequence of the pseudo site is shown in bold. Approximately 40 bp surrounding the core represent the minimal attP pseudo site.

DETAILED DESCRIPTION OF THE INVENTION

Figure 1A:
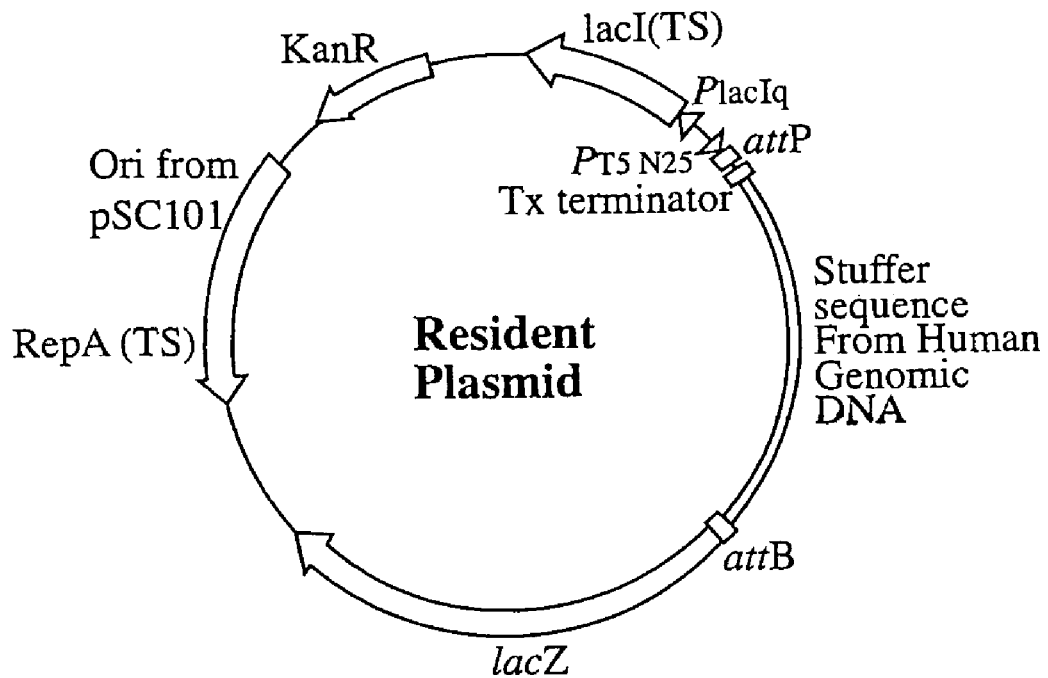
FIGS. 1A and 1B depict plasmids useful in an integrase shuffling genetic screen.

Throughout this application, various publications, patents, and published patent applications are referred to by an identifying citation. The disclosures of these publications, patents, and published patent specifications referenced in this application are hereby incorporated by reference into the present disclosure to more fully describe the state of the art to which this invention pertains.

The practice of the present invention will employ, unless otherwise indicated, conventional techniques of molecular biology, microbiology, cell biology and recombinant DNA, which are within the skill of the art. See, e.g., Sambrook, Fritsch, and Maniatis, MOLECULAR CLONING: A LABORATORY MANUAL, 2nd edition (1989); CURRENT PROTOCOLS IN MOLECULAR BIOLOGY, (F. M. Ausubel et al. eds., 1987); the series METHODS IN ENZYMOLOGY (Academic Press, Inc.); PCR 2: A PRACTICAL APPROACH (M. J. McPherson, B. D. Hames and G. R. Taylor eds., 1995) and ANIMAL CELL CULTURE (R. I. Freshney. Ed., 1987).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise. Thus, for example, reference to "a plasmid" includes a mixture of two or more such plasmids.

1. DEFINITIONS

"Recombinases" are a family of enzymes that mediate site-specific recombination between specific DNA sequences recognized by the recombinase (Esposito, D., and Scocca, J. J., Nucleic Acids Research 25, 3605–3614 (1997); Nunes-Duby, S. E., et al., Nucleic Acids Research 26, 391–406 (1998); Stark, W. M., et al., Trends in Genetics 8, 432–439 (1992)).

"Altered recombinases" refer to recombinase enzymes in which the native, wild-type recombinase gene found in the organism of origin has been mutated in one or more positions. An altered recombinase possesses a DNA binding specificity and/or level of activity that differs from that of the wild-type enzyme. Such altered binding specificity permits the recombinase to react with a given DNA sequence differently than would the native enzyme, while an altered level of activity permits the recombinase to carry out the reaction at greater or lesser efficiency. A recombinase reaction typically includes binding to the recognition sequence and performing concerted cutting and ligation, resulting in strand exchanges between two recombining recognition sites.

In particular, altered recombinases that recognize endogenous sequences in a genome of interest are one subject of the present invention. The mutations present in an altered recombinase may comprise base substitutions, deletions, additions, and/or other rearrangements in the DNA sequence encoding the recombinase, and/or any combination of such mutations, either singly or in groups. The altered recombinase may possess broader or narrower DNA recognition specificity compared to the wild-type enzyme and/or greater or lesser catalytic activity toward a particular DNA sequence, including a wild-type or non wild-type recombinase recognition site.

A "pseudo-site" is a DNA sequence recognized by a recombinase enzyme such that the recognition site differs in one or more base pairs from the wild-type recombinase recognition sequence and/or is present as an endogenous sequence in a genome that differs from the genome where the wild-type recognition sequence for the recombinase resides.

"Pseudo attP site" or "pseudo attB site" refer to pseudo sites that are similar to wild-type phage or bacterial attachment site sequences, respectively, for phage integrase enzymes. "Pseudo att site" is a more general term that can refer to either a pseudo attP site or a pseudo attB site.

A recombination site "native" to the genome, as used herein, means a recombination site that occurs naturally in the genome of a cell (i.e., the sites are not introduced into the genome, for example, by recombinant means.)

By "nucleic acid construct" it is meant a nucleic acid sequence that has been constructed to comprise one or more functional units not found together in nature. Examples include circular, double-stranded, extrachromosomal DNA molecules (plasmids), cosmids (plasmids containing COS sequences from lambda phage), viral genomes comprising non-native nucleic acid sequences, and the like.

By "nucleic acid fragment of interest" it is meant any nucleic acid fragment that one wishes to insert into a genome. Suitable examples of nucleic acid fragments of interest include therapeutic genes, marker genes, control regions, trait-producing fragments, and the like.

"Therapeutic genes" are those nucleic acid sequences which encode molecules that provide some therapeutic benefit to the host, including proteins, functional RNAs (antisense, hammerhead ribozymes), and the like. One well known example is the cystic fibrosis transmembrane conductance regulator (CFTR) gene. The primary physiological defect in cystic fibrosis is the failure of electrogenic chloride ion secretion across the epithelia of many organs, including the lungs. One of the most dangerous aspects of the disorder is the cycle of recurrent airway infections which gradually destroy lung function resulting in premature death. Cystic fibrosis is caused by a variety of mutations in the CFTR gene. Since the problems arising in cystic fibrosis result from mutations in a single gene, the possibility exists that the introduction of a normal copy of the gene into the lung epithelia could provide a treatment for the disease, or effect a cure if the gene transfer was permanent.

Other disorders resulting from mutations in a single gene (known as monogenic disorders) include alpha-1-antitrypsin deficiency, chronic granulomatous disease, familial hypercholesterolemia, Fanconi anemia, Gaucher disease, Hunter syndrome, ornithine transcarbamylase deficiency, purine nucleoside phosphorylase deficiency, severe combined immunodeficiency disease (SCID)-ADA, X-linked SCID, hemophilia, and the like.

Therapeutic benefit in other disorders may also result from the addition of a protein-encoding therapeutic nucleic acid. For example, addition of a nucleic acid encoding an immunomodulating protein such as interleukin-2 may be of therapeutic benefit for patients suffering from different types of cancer.

A nucleic acid fragment of interest may additionally be a "marker nucleic acid" or "marker polypeptide". Marker genes encode proteins which can be easily detected in transformed cells and are, therefore, useful in the study of those cells. Marker genes are being used in bone marrow transplantation studies, for example, to investigate the biology of marrow reconstitution and the mechanism of relapse in patients. Examples of suitable marker genes include beta-galactosidase, green or yellow fluorescent proteins, chloramphenicol acetyl transferase, luciferase, and the like.

A nucleic acid fragment of interest may additionally be a control region. The term "control region" or "control element" includes all nucleic acid components which are operably linked to a nucleic acid fragment (e.g., DNA) and involved in the expression of a protein or RNA therefrom. The precise nature of the control (or regulatory) regions needed for coding sequence expression may vary from organism to organism. Such regions typically include those 5' noncoding sequences involved with initiation of transcription and translation, such as the enhancer, TATA box, capping sequence, CAAT sequence, and the like. Further exemplary control sequences include, but are not limited to, any sequence that functions to modulate replication, transcriptional or translational regulation, and the like. Examples include promoters, signal sequences, propeptide sequences, transcription terminators, polyadenylation sequences, enhancer sequences, attenuatory sequences, intron splice site sequences, and the like.

A nucleic acid fragment of interest may additionally be a trait-producing sequence, by which it is meant a sequence conferring some non-native trait upon the organism or cell in which the protein encoded by the trait-producing sequence is expressed. The term "non-native" when used in the context of a trait-producing sequence means that the trait produced is different than one would find in an unmodified organism which can mean that the organism produces high amounts of a natural substance in comparison to an unmodified organism, or produces a non-natural substance. For example, the genome of a crop plant, such as corn, can be modified to produce higher amounts of an essential amino acid, thus creating a plant of higher nutritional quality, or could be modified to produce proteins not normally produced in plants, such as antibodies. (See U.S. Pat. No. 5,202,422 (issued Apr. 13, 1993); U.S. Pat. No. 5,639,947 (Jun. 17, 1997).) Likewise, the genomes of industrially important microorganisms can be modified to make them more useful such as by inserting new metabolic pathways with the aim of producing novel metabolites or improving both new and existing processes such as the production of antibiotics and industrial enzymes. Other useful traits include herbicide resistance, antibiotic resistance, disease resistance, resistance to adverse environmental conditions (e.g., temperature, pH, salt, drought), and the like.

Methods of transforming cells are well known in the art. By "transformed" it is meant a heritable alteration in a cell resulting from the uptake of foreign DNA. Suitable methods include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term polynucleotide sequence is the alphabetical representation of a polynucleotide molecule. This alphabetical representation can be input into databases in a computer having a central processing unit and used for bioinformatics applications such as functional genomics and homology searching.

A "coding sequence" or a sequence which "encodes" a selected polypeptide, is a nucleic acid molecule which is transcribed (in the case of DNA) and translated (in the case of mRNA) into a polypeptide, for example, in vivo when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with a polypeptide encoded by the sequence.

"Operably linked" refers to an arrangement of elements wherein the components so described are configured so as to perform their usual function. Thus, a given promoter that is operably linked to a coding sequence (e.g., a reporter expression cassette) is capable of effecting the expression of the coding sequence when the proper enzymes are present. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

An "expression cassette" comprises any nucleic acid construct capable of directing the expression of a gene/coding sequence of interest. Such cassettes can be constructed into a "vector," "vector construct," "expression vector," or "gene transfer vector," in order to transfer the expression cassette into target cells. Thus, the term includes cloning and expression vehicles, as well as viral vectors.

Techniques for determining nucleic acid and amino acid "sequence identity" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482–489 (1981). This algorithm can be applied to amino acid sequences by using the scoring matrix developed by Dayhoff, *Atlas of Protein Sequences and Structure*, M. O. Dayhoff ed., 5 suppl. 3:353–358, National Biomedical Research Foundation, Washington, D.C., USA, and normalized by Gribskov, *Nucl. Acids Res.* 14(6):6745–6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+ PDB+GenBank CDS translations+Swiss protein+Spupdate+ PIR. Details of these programs can be found at the following internet address: the world wide website of the National Center for Biotechnology Information.

Alternatively, homology can be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%–85%, preferably at least about 85%–90%, more preferably at least about 90%–95%, and most preferably at least about 95%–98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10–14 nucleotides in length having at least approximately 70% sequence identity with the sequence of the selected nucleic acid probe. Stringent hybridization conditions typically allow detection of target nucleic acid sequences of at least about 10–14 nucleotides in length having a sequence identity of greater than about 90–95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.)

A first polynucleotide is "derived from" a second polynucleotide if it has the same or substantially the same basepair sequence as a region of the second polynucleotide, its cDNA, complements thereof, or if it displays sequence identity as described above.

A first polypeptide is "derived from" a second polypeptide if it is (i) encoded by a first polynucleotide derived from a second polynucleotide, or (ii) displays sequence identity to the second polypeptides as described above.

In the present invention, when a recombinase is "derived from a phage" the recombinase need not be explicitly produced by the phage itself, the phage is simply considered to be the original source of the recombinase and coding sequences thereof. Recombinases can, for example, be produced recombinantly or synthetically, by methods known in the art, or alternatively, recombinases may be purified from phage infected bacterial cultures.

"Substantially purified" general refers to isolation of a substance (compound, polynucleotide, protein, polypeptide, polypeptide composition) such that the substance comprises the majority percent of the sample in which it resides. Typically in a sample a substantially purified component comprises 50%, preferably 80%–85%, more preferably 90–95% of the sample. Techniques for purifying polynucleotides and polypeptides of interest are well-known in the art and include, for example, ion-exchange chromatography, affinity chromatography and sedimentation according to density.

2. Modes of Carrying Out The Invention

A. General Overview of the Invention

In order to make more efficient use of site-specific recombinases, such as phage integrases, for genome modification, their sequence recognition properties are altered so that they effectively recognize pseudo-site sequences present in eukaryotic genomes of interest at desirable locations. These pseudo-site sequences are then used as locations for chromosomal integration and stable expression of introduced DNA. This disclosure identifies methods to alter the specificity of recombinases such as the φC31 integrase, so that these altered recombinases can be used in genetic engineering of the chromosomes of higher cells. Such genomic modifications are useful for generating transgenic cells, tissues, animals, and plants, and are also useful in gene therapy techniques.

In one aspect, the invention disclosed herein provides a method to obtain site-specific integration into a target genome of interest. In this method, a DNA sequence of interest is present on a circular DNA molecule that possesses a recognition site for an altered recombinase. This DNA is introduced into a cell along with the altered recombinase. Site-specific recombination takes place between the circular DNA molecular possessing a recognition site for the altered recombinase and a native DNA sequence present in the cellular genome that is also recognized by the altered recombinase, resulting in site-specific integration of the DNA sequence of interest into the cellular genome.

Alternatively, site-specific recombination can take place between the circular DNA molecule possessing a recognition site for the altered recombinase and a recognition site, either a wild-type att site or a pseudo att site, that has been inserted into the genome. Such placement of a recognition site has utility for use as a target for further integration events mediated by the altered site-specific recombinase.

Because of the rarity of naturally occurring pseudo-sites that possess sufficient efficacy and favorable location, the ability to alter the specificity and/or efficiency of recombinase enzymes to access desired integration locations in target genomes (e.g., genomes of higher eucaryotes) is important for efficient use of a recombinase strategy of genome modification. In such strategies, recombinases, such as the integrase of bacteriophage φC31 which perform unidirectional recombination between non-identical attachment sites and do not require host cofactors (Thorpe, H. M., and Smith, M. C. M., Proc. Natl. Acad. Sci. USA 95, 5505–5510 (1998); Thorpe, H. M., et al., Molecular Microbiology 38, 232–241 (2000.)), are particularly useful.

Binding sites for phage integrase enzymes, such as the φC31 integrase, are traditionally called attB and attP (i.e., the target sites of the integrase). These sites have a minimal length of approximately 34–40 base pairs (bp) (Groth, A. C., et al., Proc. Natl. Acad. Sci. USA 97, 5995–6000 (2000)).

These sites are typically arranged as follows: AttB comprises a first DNA sequence attB5', a core region, and a second DNA sequence attB3' in the relative order attB5'-core region-attB3', (ii) attP comprises a first DNA sequence (attP5'), a core region, and a second DNA sequence (attP3') in the relative order attP5'-core region-attP3', and (iii) wherein the recombinase mediates production of recombination-product sites that can no longer act as a substrate for the recombinase, the recombination-product sites comprising, for example, the relative order attB5'-recombination-product site-attP3' and attP5'-recombination-product site-attB3'. In the practice of the present invention, such integrases are altered so that they recognize native, e.g., genomic sequences that are related to either the natural attB or attP target sites of the unmodified recombinase. Accordingly, target sequences for an altered recombinase are called pseudo att sites. Such pseudo att sites are present in cellular genomes where integration is desired.

Accordingly, in one embodiment, the present invention is directed to a method of site-specifically integrating a polynucleotide sequence of interest in a genome of a eucaryotic cell. The method comprises introducing (i) a circular targeting construct, comprising a first recombination site and the polynucleotide sequence of interest, and (ii) an altered, site-specific recombinase into the eucaryotic cell, wherein the genome of the cell comprises a second recombination site (i.e., a pseudo att site) native to the genome and recombination between the first and second recombination sites is facilitated by the altered, site-specific recombinase. The cell is maintained under conditions that allow recombination between the first and second recombination sites and the recombination is mediated by the altered, site-specific recombinase. The result of the recombination is site-specific integration of the polynucleotide sequence of interest in the genome of the eucaryotic cell.

The altered recombinase may be introduced into the cell before, concurrently with, or after introducing the circular targeting construct. Further, the circular targeting construct may comprise other useful components, such as a bacterial origin of replication and/or a selectable marker.

In yet further embodiments, the altered, site-specific is recombinase is a recombinase originally encoded by a phage selected from the group consisting of φC31, TP901-1, and R4 (a "parent" recombinase; e.g., φC31, Kuhstoss and Rao, J. Mol. Biol. 222:897–908, 1991; TP901-1, Christiansen, et al., J. Bact. 178:5164–5173, 1996; R4, Matsuura, et al., J. Bact. 178:3374–3376, 1996). Altered recombinases may be generated from each of these recombinases by the methods described herein. Further, altered recombinases that combine sequences from different parent recombinases may also be generated and their activities optimized by the methods described herein. The full length φC31 attP and attB sites are shown in FIGS. 11A and 11B. The R4 attB and attP sites are shown in FIGS. 12A and 12B.

The altered recombinase may facilitate recombination between a first and second recombination site, for example, as follows: (a) a bacterial genomic recombination site (attB) and a pseudo phage genomic recombination site (pseudo-attP); (b) a pseudo-attB site and an attP site; or (d) a pseudo-attB site and a pseudo-attP site. These sites may be described as follows for either the naturally occurring or pseudo-sequences.

The altered recombinase may be introduced into the target cell as a polypeptide. In alternative embodiments, the altered recombinase is introduced into the cell as a polynucleotide encoding the altered recombinase and an expression cassette, optionally carried on a transient expression vector, which comprises the polynucleotide encoding the recombinase.

In another embodiment, the invention is directed to a vector for site-specific integration of a polynucleotide sequence into the genome of a eucaryotic cell. The vector comprises (i) a circular backbone vector, (ii) a polynucleotide of interest operably linked to a eucaryotic promoter, and (iii) a first recombination site, wherein the genome of the cell comprises a second recombination site native to the genome and recombination between the first and second recombination sites is facilitated by an altered recombinase.

B. Recombination Sites

The inventors have discovered native recombination sites existing in the genomes of a variety of organisms, where the native recombination site does not necessarily have a nucleotide sequence identical to the wild-type recombination sequences (for a given recombinase); but such native recombination sites are nonetheless sufficient to promote recombination meditated by the recombinase. Such recombination site sequences are referred to herein as "pseudo-recombination sequences."

In the practice of the present invention, wild-type recombination sites and pseudo-recombination sites may be employed in the generation of altered recombinases. See, e.g., Examples 1 and 2.

Identification of pseudo-recombination sequences can be accomplished, for example, by using sequence alignment and analysis, where the query sequence is the recombination site of interest (for example, attP and/or attB).

The genome of a target cell may-searched for sequences having sequence identity to the selected recombination site for a given recombinase, for example, the attP and/or attB of φC31 or R4 (e.g., FIGS. 11A, 11B, 11C, 12A and 12B) Nucleic acid sequence databases, for example, may be searched by computer. The findpatterns algorithm of the Wisconsin Software Package Version 9.0 developed by the Genetics Computer Group (GCG; Madison, Wis.), is an example of a programmed used to screen all sequences in the GenBank database (Benson et al., 1998, Nucleic Acids Res. 26, 1–7). In this aspect, when selecting pseudo-recombination sites in a target cell, the genomic sequences of the target cell can be searched for suitable pseudo-recombination sites using either the attp or attb sequences associated with a particular recombinase or altered recombinase. Functional sizes and the amount of heterogeneity that can be tolerated in these recombination sequences can be empirically evaluated, for example, by evaluating integration efficiency of a targeting construct using an altered recombinase of the present invention (for exemplary methods of evaluating integration events, see, WO 00/11155, published 2 Mar. 2000).

Functional pseudo-sites can also be found empirically. For example, experiments performed in support of the present invention have shown that after co-transfection into human cells of a plasmid carrying φC31 attB and the neomycin resistance gene, along with a plasmid expressing the φC31 integrase, an elevated number of neomycin resistant colonies are obtained, compared to co-transfections in which either attB or the integrase gene were omitted. Most of these colonies reflected integration into native pseudo attP sites. Such sites are recovered, for example, by plasmid rescue and analyzed at the DNA sequence level, producing, for example, the DNA sequence of a pseudo attP site from the human genome, such as ψA (FIG. 13). This empirical method for identification of pseudo-sites can be used, even if a detailed knowledge of the recombinase recognition sites and the nature of recombinase binding to them are unknown.

When a pseudo-recombination site is identified (using either attP or attB search sequences) in a target genome (such as human or mouse), that pseudo-recombination site can be used in the methods of the present invention to generate an altered recombinase. For example, such a pseudo-recombination site could be used as either the attP or attB site in the resident vector shown in FIG. 1A.

Then attP or attB sites corresponding to the pseudo-recombination sites can be used in the targeting construct to be employed with an altered recombinase. For example, if attP for a selected recombinase is used to identify a pseudo-recombination site in the target cell genome, then the wild-type attB sequence can be used in the targeting construct. In an alternative example, if attB for a selected recombinase is used to identify a pseudo-recombination site in the target cell genome, then the wild-type attP sequence can be used in the targeting construct.

The targeting constructs contemplated by the invention may contain additional nucleic acid fragments such as control sequences, marker sequences, selection sequences and the like as discussed below.

In one aspect of the present invention, the native recombinase (for example, φC31) recognizes a recombination site where sequence of the 5' region of the recombination site can differ from the sequence of the 3' region of the recombination sequence (φC31, Kuhstoss, S., and Rao, R. N., J. Mol. Biol. 222, 897–908 (1991)). For example, for the phage φC31 attP (the phage attachment site), the core region is 5'-TTG-3' the flanking sequences on either side are represented here as attP5' and attP3', the structure of the attP recombination site is, accordingly, attP5'-TTG-attP3'. Correspondingly, for the native bacterial genomic target site (attB) the core region is 5'-TTG-3', and the flanking sequences on either side are represented here as attB5' and attB3', the structure of the attB recombination site is, accordingly, attB5'-TTG-attB3'. After a single-site, φC31 integrase mediated, recombination event takes place the result is the following recombination product: attB5'-TTG-attP3' {C31 vector sequences}attP5'-TTG-attB3'. Typically, after recombination the post-recombination recombination sites are no longer able to act as substrate for the φC31 recombinase. This results in stable integration with little or no recombinase mediated excision.

C. Altered Recombinases

The study of protein structure and function, as well as methods to alter proteins have advanced in recent years. Attractive strategies for generating and screening altered enzymes have produced impressive results. In particular, the strategy of generating large pools of variants of a protein and screening them for a desired function has been productive.

These strategies have not been applied extensively to alter the specificity of enzymes that recognize DNA sequence. In terms of recombinase enzymes, Cre recombinase and its relative FLP have been the subject of a few modification studies. For example, random variants of FLP were selected that functioned better at 37° C. than the native enzyme (Buchholz, F., et al., Nature Biotechnology 16, 657–662 (1998)). Directed variants in Cre with altered DNA binding properties have also been produced (Hartung, M., and Kisters-Woike, B. J. Biol. Chem. 273, 22884–22891<(1998)). Mutations that change the binding specificity of phage λ integrase to that of the closely related phage HK022 integrase have also been reported (Dorgai, L., et al., J. Molec. Biol. 22, 178–188 (1995); Yagil, E., et al., J. Molec. Biol. 252, 163–177 (1995). In no case has the DNA binding specificity of a recombinase been changed to match that of an endogenous eukaryotic genomic sequence.

An attractive strategy for altering proteins that has been effective is the DNA shuffling protocol developed by Stemmer. This strategy maximizes the number of variants, or altered proteins, that can be screened (Stemmer, W. P. C., Proc. Natl. Acad. Sci. USA 91, 10747–10751 (1994); Stemmer, W. P. C., Nature 370, 389–391 (1994)). A large pool of variants of the gene of interest is generated by a procedure including DNaseI fragmentation, followed by shuffling and reassembly by PCR.

The shuffling protocol appears to be more effective than other approaches, because it involves recombination of blocks of sequences between many molecules, each bearing different mutations. The method is therefore combinatorial and samples a much larger sequence space than merely linear methods such as error-prone PCR or cassette mutagenesis. (See, for example, the following U.S patents: U.S. Pat. No. 5,605,793, Methods for in vitro recombination; U.S. Pat. No. 5,811,238, Methods for generating polynucleotides having desired characteristics by iterative selection and recombination; U.S. Pat. No. 5,830,721, DNA mutagenesis by random fragmentation and reassembly; U.S. Pat. No. 6,117,679, Methods for generating polynucleotides having desired characteristics by iterative selection and recombination.)

To perform DNA shuffling, the gene of interest is first amplified by PCR. This pool of fragments is then digested with DnaseI to produce random fragments. A collection of such fragments, for example of 10–50 bp in length, is then subjected to PCR without added primers. Regions of homology within the fragments anneal and serve to prime the PCR reaction, resulting in reassembly of the gene. Primers are then added to collect reassembled products, which are cloned to form the shuffled library. This library contains a wide variety of sequence combinations, patched together from all the underlying mutations present in the PCR fragments. The procedure is very effective for creating a very diverse pool of molecules carrying blocks of sequence derived from different parent molecules. It is particularly effective in situations where complex changes in protein structure and/or behavior are required, which would be difficult to design rationally.

Sequences from single or multiple sources may be shuffled (see Examples 1 and 4).

In the present invention, such shuffling protocols have been used to generate altered recombinases. Of importance in this invention is use of the shuffling protocol in combination with an effective genetic screen to identify desired altered recombinases.

Methods for obtaining altered integrases are described in the examples. Other integrases in addition to that of phage φC31 serve as substrates for the shuffling and screening protocols. Experiments performed in support of the present invention have shown that the integrases from phages R4 (Matsuura, M., et al., J. Bacteriology 178, 3374–3376 (1996); Shirai, M., et al., J. Bacteriology 173, 4237–4239 (1991)) and TP901 (Brondsted, L., and Hammer, K., Applied and Environmental Microbiology 65, 752–758 (1999); Christiansen, B., et al., J. Bacteriology 178, 5164–5173 (1996); Christiansen, B., et al., J. Bacteriology 176, 1069–1076 (1994)) work well in human cells. These integrases and others like them can be altered by the methods of the present invention.

Experiments performed in support of the present invention have demonstrated that pseudo att sites, sequences similar to attB and attP for phage integrase enzymes, exist in the human and mouse genomes. Specifically, it has been shown that the phage φC31 recombinase mediates efficient integration in the human cell environment at attB and attP phage attachment sites on extrachomosomal vectors. Further, experiments performed in support of the present invention have demonstrated that phage attP sites inserted at various locations in human and mouse chromosomes serve as efficient targets for precise site-specific integration. Moreover, psuedo-attP sites in the human and mouse genomes were also shown to mediate efficient recombinase-mediated integration. Such genomic sites were shown to have partial sequence identity to attP. These sites constitute naturally occurring integration targets. However, integration frequencies at such genomic sites suggest that they may have a lower affinity for integrases than do wild-type att sites.

These studies revealed that there exists a hierarchy of native sequences in target genomes that are recognized by the φC31 integrase and act as sites for integrase-mediated integration of a plasmid bearing an attB site. These native sequences were recovered from genomic DNA and analyzed at the DNA sequence level. These data revealed that the genomic sites have significant identity to attP and are used by the φC31 integrase to mediate integration of a plasmid bearing an attB site. These native sequences are designated pseudo attP sites.

One of the pseudo attP sites in the human genome, called human ψA, was found to be used as an integration site preferentially. Several other human pseudo sites were also used repeatedly by the enzyme. The total number of pseudo attP sites in the human genome is not known but appears to be of the order of $10^2$.

A similar study of integration into the mouse genome gave similar results, though no one pseudo site was as predominant as human ψA (FIG. 13). These experiments verified earlier studies with the Cre recombinase (Thyagarajan, et al., Gene 244:47–54 (2000)) that suggested that site-specific recombinases with recognition sites in the range of 30–40 bp long would have native genomic sites with partial identity to the wild type recognition site that could be utilized for recombination by the enzyme. The number of pseudo attP sites in the human and mouse genomes suggests that the enzyme has potential recognition sites in many other eukaryotic genomes as well, such as those of other vertebrates, insects, worms, and plants.

These pseudo att sites and related sequences are used as starting material for the methods described below to generate altered recombinases. The methods disclosed herein produce novel altered integrase enzymes having enhanced or decreased specificity for a chosen pseudo att site. For example, in the method described in Example 1 a pseudo att site can be used as, for example, the attB site in the resident plasmid.

In one aspect of the present invention, a genetic screen for integration efficiency in *E. coli* has been used to identify altered recombinases such as phage integrases. In an exemplary screen, the frequency of integration occurring in a bacterial colony was determined by the degree of blueness on an Xgal plate, when a particular pseudo attP or attB sequence is used as the substrate for recombination. This assay has been used to find altered integrases that preferentially recognize a particular pseudo att site in the human genome (Example 1), often at the same time losing affinity for other pseudo att sites that may be present. In this way, integration is focused on a preferred chromosomal location that has desirable properties, such as good gene expression and lack of disruption of a native gene.

In this assay, the two att sites to be tested for recombination are cloned on a plasmid that is resident in *E. coli* (FIG. 1A; Resident Plasmid). The two att sites are separated by a stuffer region containing transcription termination signals. Adjacent to the att sites is the coding region of lacZ, without a promoter. An intramolecular integration reaction restores the lac promoter to lacZ, resulting in blue color on Xgal plates. The resident plasmid carries a temperature-sensitive version of lacI and a temperature-sensitive origin of replication. Both of these elements are relatively inactive during growth at 37 degrees. In a method of the present invention, a population of cells may be provided where each cell of the population comprises a resident plasmid. As described, the resident plasmid typically comprises a promoter, functional in the cell used for screening, adjacent a first recombination site which is adjacent a transcription terminator, which is adjacent a second recombination site, which is adjacent a coding sequence of interest. Accordingly, the typical order of these components of the resident plasmid is promoter-first recombination site (e.g., attP or corresponding pseudo-site)-transcription terminator (one or more transcription termination sequence effective to block read-through transcription)-second recombination site (e.g., attB or corresponding pseudo-site)-coding sequence of interest (e.g., a marker or selection coding sequence). The coding sequence of interest may encode a number of different products (e.g., a functional RNA and/or a polypeptide, see below). The product produced from the coding sequence of interest is used for screening and/or selection.

Figure 1B:
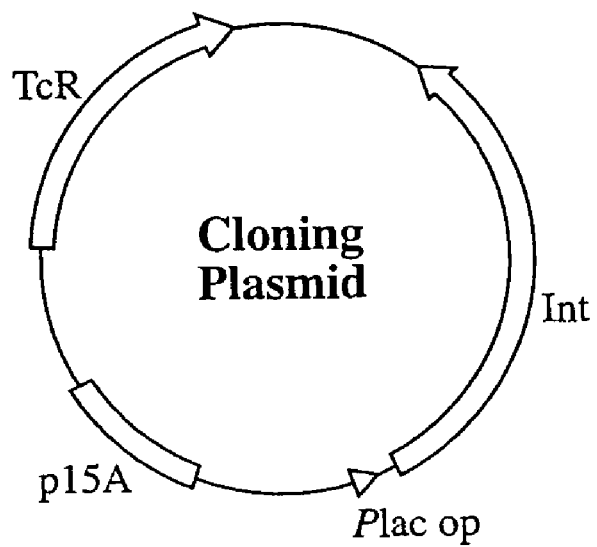

The cloning plasmid (FIG. 1B; Cloning Plasmid) is the recipient for shuffled integrase genes and produces integrase when its lac promoter is unrepressed. Accordingly, the cloning plasmid is usually a population (or group) of plasmids, each plasmid containing at least one shuffled integrase gene, where multiple different shuffled genes are represented in the group. The shuffled gene (i.e., altered recombinase) is operably linked to a promoter that is functional in the target cell being used for the screen.

To perform the assay, a recombinase (e.g., phage integrase) fragment is isolated and subjected to shuffling. To shuffle, for example, a restriction fragment carrying the gene is gel purified and digested with DNaseI. Fragments of 10–50 bp are gel purified and subjected to multiple cycles of PCR without primers. Finally, PCR with primers is carried out. The resulting pool of mutated integrase genes is ligated into the cloning plasmid. The ligation mix is transformed into bacteria containing the resident plasmid, and the transformed cells maintained under appropriate conditions, for example, spread on plates containing kanamycin, tetracyline, and Xgal, and grown at 30 degrees. Under these conditions, the integrase gene is not expressed, because lac repressor is active and will repress the lac promoter controlling the integrase gene by binding to the lac operator. Transformed cells are grown for approximately 24 hours until moderately sized colonies are obtained.

The plates are then placed at 37 degrees for various periods of time. Under these conditions, the resident plasmid does not replicate and integrase is expressed, due to the temperature lability of the lacI gene product (lac repressor) and the plasmid repA replication protein. Under these static conditions, progress of the intramolecular integration reaction is monitored by following expression of lacZ, as manifested by blue color on the Xgal plates.

Figure 2:
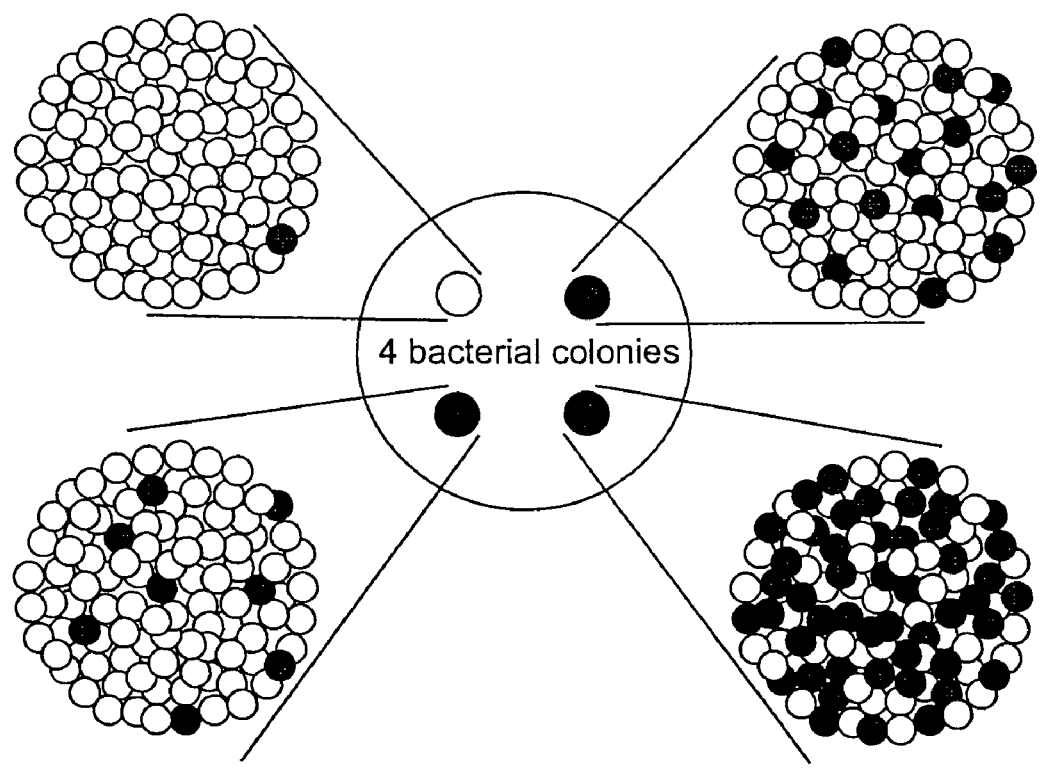
FIG. 2 schematically illustrates an assay for altered recombinases by coloration of colonies on Xgal plates.

Different levels of integration produce different patterns of coloration in the resulting colonies, depending on the timing and frequency of integration events. Schematically represented exemplary results are shown in FIG. 2. These patterns give a measure of the ability of altered integrase enzymes to recognize variant pseudo att sites.

The bluest colonies are typically pooled and plasmid DNA purified. Integrase gene fragments from this pool are subjected to further rounds of shuffling and the screening assay repeated for each round. In this way the affinity of the altered integrase for the desired pseudo att site is progressively increased. The methods described herein allow the identification of coding sequences for altered recombinases.

Altered recombinases produced by the above method are described in Example 1. The screening assay for improved integrases was performed in *E. coli*. The altered integrases emerging from this screen were tested in human cells to determine if the desirable properties detected in bacteria were retained. The wild-type φC31 integrase and the 1C1 integrase mutant described in Example 1 were compared to each other in mammalian tissue culture cells for their ability to mediate the integration of a plasmid carrying the attB recognition site (FIG. 11B; SEQ ID NO:30) and the neomycin resistance gene into human chromosomes. Integration specific for the ψA site was demonstrated (Examples 1 and 2).

Other screening methods useful in the practice of the present invention are described in the examples. Altered recombinases generated by the methods of the present invention typically provide an increased recombination frequency between target recombination sites relative to the parent recombinase(s); although the methods described herein may also be used to identify altered recombinases providing reduced or similar recombination frequencies between target recombination sites relative to the recombination frequency provided by the parent recombinase(s).

D. Targeting Constructs and Methods of the Present Invention

The present invention also provides means for targeted insertion of a polynucleotide (or nucleic acid sequence(s)) of interest into a genome by, for example, (i) providing an altered recombinase, wherein the altered recombinase is capable of facilitating recombination between a first recombination site and a second recombination site, (ii) providing a targeting construct having a first recombination sequence and a polynucleotide of interest, (iii) introducing the altered recombinase and the targeting construct into a cell which contains in its nucleic acid the second recombination site, wherein said introducing is done under conditions that allow the altered recombinase to facilitate a recombination event between the first and second recombination sites.

Historically, the attachment site in a bacterial genome is designated "attB" and in a corresponding bacteriophage the site is designated "attP". In one aspect of the present invention, at least one pseudo-recombination site for a selected, altered recombinase is identified in a target cell of interest. These sites can be identified by several methods including searching all known sequences derived from the cell of interest against a wild-type recombination site (e.g., attb or attp) for a selected, altered recombinase (e.g., as described above). The functionality of pseudo-recombination sites identified in this way can then be empirically evaluated following the teachings of the present specification to determine their ability to participate in a recombinase-mediated recombination event.

A targeting construct, to direct integration to a pseudo-recombination site, would then comprise a recombination site wherein the altered recombinase can facilitate a recombination event between the recombination site in the genome of the target cell and a recombination site in the targeting construct. A targeting vector may further comprise a polynucleotide of interest. Polynucleotides of interest can include, but are not limited to, expression cassettes encoding polypeptide products. The targeting constructs are typically circular and may also contain selectable markers, an origin of replication, and other elements. Targeting constructs of the present invention are typically circular.

A variety of expression vectors are suitable for use in the practice of the present invention, both for prokaryotic expression and eukaryotic expression. In general, the targeting construct will have one or more of the following features: a promoter, promoter-enhancer sequences, a selection marker sequence, an origin of replication, an inducible element sequence, an epitope-tag sequence, and the like.

Promoter and promoter-enhancer sequences are DNA sequences to which RNA polymerase binds and initiates transcription. The promoter determines the polarity of the transcript by specifying which strand will be transcribed. Bacterial promoters consist of consensus sequences, −35 and −10 nucleotides relative to the transcriptional start, which are bound by a specific sigma factor and RNA polymerase. Eukaryotic promoters are more complex. Most promoters utilized in expression vectors are transcribed by RNA polymerase II. General transcription factors (GTFS) first bind specific sequences near the start and then recruit the binding of RNA polymerase II. In addition to these minimal promoter elements, small sequence elements are recognized specifically by modular DNA-binding/trans-activating proteins (e.g. AP-1, SP-1) that regulate the activity of a given promoter. Viral promoters serve the same function as bacterial or eukaryotic promoters and either provide a specific RNA polymerase in trans (bacteriophage T7) or recruit cellular factors and RNA polymerase (SV40, RSV, CMV). Viral promoters may be preferred as they are generally particularly strong promoters.

Promoters may be, furthermore, either constitutive or regulatable. Inducible elements are DNA sequence elements which act in conjunction with promoters and may bind either repressors (e.g. lacO/LAC Iq repressor system in *E. coli*) or inducers (e.g. gal1/GAL4 inducer system in yeast). In such cases, transcription is virtually "shut off" until the promoter is derepressed or induced, at which point transcription is "turned-on."

Examples of constitutive promoters include the int promoter of bacteriophage λ, the bla promoter of the β-lactamase gene sequence of pBR322, the CAT promoter of the chloramphenicol acetyl transferase gene sequence of pPR325, and the like. Examples of inducible prokaryotic promoters include the major right and left promoters of bacteriophage ($P_L$ and $P_R$), the trp, reca, lacZ, AraC and gal promoters of *E. coli*, the α-amylase (Ulmanen, et al., J. Bacteriol. 162:176–182, 1985) and the sigma-28-specific promoters of *B. subtilis* (Gilman et al., Gene 32:11–20 (1984)), the promoters of the bacteriophages of *Bacillus* (Gryczan, In: The Molecular Biology of the Bacilli, Academic Press, inc., NY (1982)), *Streptomyces* promoters (Ward et at., Mol. Gen. Genet. 203:468–478, 1986), and the like. Exemplary prokaryotic promoters are reviewed by Glick (J. Ind. Microtiot. 1:277–282, 1987); Cenatiempo (Biochimie 68:505–516, 1986); and Gottesman (Ann. Rev. Genet. 18:415–442, 1984).

Preferred eukaryotic promoters include, but are not limited to, the following: the promoter of the mouse metallothionein I gene sequence (Hamer et al., J. Mol. Appl. Gen. 1:273–288, 1982); the TK promoter of Herpes virus (McKnight, Cell 31:355–365, 1982); the SV40 early promoter (Benoist et al., Nature (London) 290:304–310, 1981); the yeast gall gene sequence promoter (Johnston et al., Proc. Natl. Acad. Sci. (USA) 79:6971–6975, 1982); Silver et al., Proc. Natl. Acad. Sci. (USA) 81:5951–59SS, 1984), the CMV promoter, the EF-1 promoter, Ecdysone-responsive promoter(s), tetracycline-responsive promoter, and the like.

Exemplary promoters for use in the present invention are selected such that they are functional in the cell type (and/or animal or plant) into which they are being introduced.

Selection markers are valuable elements in expression vectors as they provide a means to select for growth of only those cells that contain a vector. Such markers are typically of two types: drug resistance and auxotrophic. A drug resistance marker enables cells to detoxify an exogenously added drug that would otherwise kill the cell. Auxotrophic markers allow cells to synthesize an essential component (usually an amino acid) while grown in media that lacks that essential component.

Common selectable marker genes include those for resistance to antibiotics such as ampicillin, tetracycline, kanamycin, bleomycin, streptomycin, hygromycin, neomycin, Zeocin™, G418, and the like. Selectable auxotrophic genes include, for example, hisD, that allows growth in histidine free media in the presence of histidinol.

A further element useful in an expression vector is an origin of replication. Replication origins are unique DNA segments that contain multiple short repeated sequences that are recognized by multimeric origin-binding proteins and that play a key role in assembling DNA replication enzymes at the origin site. Suitable origins of replication for use in expression vectors employed herein include *E. coli* oriC, colE1 plasmid origin, 2μ and ARS (both useful in yeast systems), SV40, and EBV oriP (useful in mammalian systems), and the like.

Epitope tags are short peptide sequences that are recognized by epitope specific antibodies. A fusion protein comprising a recombinant protein and an epitope tag can be simply and easily purified using an antibody bound to a chromatography resin. The presence of the epitope tag furthermore allows the recombinant protein to be detected in subsequent assays, such as Western blots, without having to produce an antibody specific for the recombinant protein itself. Examples of commonly used epitope tags include V5, glutathione-S-transferase (GST), hemaglutinin (HA), the peptide Phe-His-His-Thr-Thr, chitin binding domain, and the like.

A further useful element in an expression vector is a multiple cloning site or polylinker. Synthetic DNA encoding a series of restriction endonuclease recognition sites is inserted into a plasmid vector, for example, downstream of the promoter element. These sites are engineered for convenient cloning of DNA into the vector at a specific position.

The foregoing elements can be combined to produce expression vectors suitable for use in the methods of the invention. Those of skill in the art would be able to select and combine the elements suitable for use in their particular system in view of the teachings of the present specification. Suitable prokaryotic vectors include plasmids such as those capable of replication in *E. coli* (for example, pBR322, ColE1, pSC101, PACYC 184, itVX, pRSET, pBAD (Invitrogen, Carlsbad, Calif.) and the like). Such plasmids are disclosed by Sambrook (cf. "Molecular Cloning: A Laboratory Manual," second edition, edited by Sambrook, Fritsch, & Maniatis, Cold Spring Harbor Laboratory, (1989)) and many such vectors are commercially available. *Bacillus* plasmids include pCl94, pC221, pT127, and the like, and are disclosed by Gryczan (In: The Molecular Biology of the Bacilli, Academic Press, NY (1982), pp. 307–329). Suitable *Streptomyces* plasmids include pli101(Kendall et al., J.

Bacteriol. 169:4177–4183, 1987), and *streptomyces* bacteriophages such as φC31 (Chater et al., In: Sixth International Symposium on Actinomycetales Biology, Akademiai Kaido, Budapest, Hungary (1986), pp. 45–54). *Pseudomonas* plasmids are reviewed by John et al. (Rev. Infect. Dis. 8:693–704, 1986), and Izaki (Jpn. J. Bacteriol. 33:729–742, 1978).

Suitable eukaryotic plasmids include, for example, BPV, EBV, vaccinia, SV40, 2-micron circle, pcDNA3.1, pcDNA3.1/GS, pYES2/GS, pMT, p IND, pIND(Spl) pVgRXR (Invitrogen), and the like, or their derivatives. Such plasmids are well known in the art (Botstein et al., Miami Wntr. SyTnp. 19:265–274, 1982; Broach, In: "The Molecular Biology of the Yeast *Saccharomyces*: Life Cycle and Inheritance", Cold Spring Harbor Laboratory, Cold Spring Harbor, N.Y., p. 445–470, 1981; Broach, Cell 28:203–204, 1982; Dilon et at., J. Clin. Hematol. Oncol. 10:39–48, 1980; Maniatis, In: Cell Biology: A Comprehensive Treatise, Vol. 3, Gene Sequence Expression, Academic Press, NY, pp. 563–608, 1980.

The targeting cassettes described herein can be constructed utilizing methodologies known in the art of molecular biology (see, for example, Ausubel or Maniatis) in view of the teachings of the specification. As described above, the targeting constructs are assembled by inserting, into a suitable vector backbone, a recombination site, polynucleotides encoding sequences of interest operably linked to a promoter of interest; and, optionally a sequence encoding a positive selection marker.

A preferred method of obtaining polynucleotides, including suitable regulatory sequences (e.g., promoters) is PCR. General procedures for PCR are taught in MacPherson et al., PCR: A PRACTICAL APPROACH, (IRL Press at Oxford University Press, (1991)). PCR conditions for each application reaction may be empirically determined. A number of parameters influence the success of a reaction. Among these parameters are annealing temperature and time, extension time, Mg2+ and ATP concentration, pH, and the relative concentration of primers, templates and deoxyribonucleotides. After amplification, the resulting fragments can be detected by agarose gel electrophoresis followed by visualization with ethidium bromide staining and ultraviolet illumination.

The expression cassettes, targeting constructs, vectors, altered recombinases and altered recombinase-coding sequences of the present invention can be formulated into kits. Components of such kits can include, but are not limited to, containers, instructions, solutions, buffers, disposables, and hardware.

E. Introducing Recombinases Into Cells

In the methods of the invention a site-specific, altered recombinase is introduced into a cell whose genome is to be modified. Methods of introducing functional proteins into cells are well known in the art. Introduction of purified altered recombinase protein ensures a transient presence of the protein and its function, which is often a preferred embodiment.

Alternatively, a gene encoding the altered recombinase can be included in an expression vector used to transform the cell. It is generally preferred that the altered recombinase be present for only such time as is necessary for insertion of the nucleic acid fragments into the genome being modified. Thus, the lack of permanence associated with most expression vectors is not expected to be detrimental.

The altered recombinases used in the practice of the present invention can be introduced into a target cell before, concurrently with, or after the introduction of a targeting vector. The altered recombinase can be directly introduced into a cell as a protein, for example, using liposomes, coated particles, or microinjection. Alternately, a polynucleotide encoding the altered recombinase can be introduced into the cell using a suitable expression vector. The targeting vector components described above are useful in the construction of expression cassettes containing sequences encoding a altered recombinase of interest. Expression of the altered recombinase is typically desired to be transient. Accordingly, vectors providing transient expression of the recombinase are preferred in the practice of the present invention. However, expression of the altered recombinase may be regulated in other ways, for example, by placing the expression of the recombinase under the control of a regulatable promoter (i.e., a promoter whose expression can be selectively induced or repressed).

Sequences encoding altered recombinases useful in the practice of the present invention are disclosed herein and may be obtained following the teachings of the present specification.

Altered recombinases for use in the practice of the present invention can be produced recombinantly or purified as previously described. Polypeptides having the desired recombinase activity can be purified to a desired degree of purity by methods known in the art of protein purification, including, but not limited to, ammonium sulfate precipitation, size fractionation, affinity chromatography, HPLC, ion exchange chromatography, heparin agarose affinity chromatography (e.g., Thorpe & Smith, Proc. Nat. Acad. Sci. 95:5505–5510, 1998.)

F. Cells

Cells suitable for modification employing the methods of the invention include both prokaryotic cells and eukaryotic cells, provided that the cell's genome contains a pseudo-recombination sequence recognizable by an altered recombinase of the present invention. Prokaryotic cells are cells that lack a defined nucleus. Examples of suitable prokaryotic cells include bacterial cells, mycoplasmal cells and archaebacterial cells. Particularly preferred prokaryotic cells include those that are useful either in various types of test systems or those that have some industrial utility, such as *Klebsiella oxytoca* (ethanol production), *Clostridium acetobutylicum* (butanol production), and the like (see Green and Bennet, Biotech & Bioengineering 58:215–221, 1998; Ingram, et al, Biotech & Bioengineering 58:204–206, 1998).

Suitable eukaryotic cells include both animal cells (such as, from insect, fish, bird, rodent (including mice and rats), cow, goat, rabbit, sheep, non-human primate, human, and the like) and plant cells (such as, from rice, corn, cotton, tobacco, tomato, potato, and the like). Cell types applicable to particular purposes are discussed in greater detail below.

Yet another embodiment of the invention comprises isolated genetically engineered cells. Suitable cells may be prokaryotic or eukaryotic, as discussed above. The genetically engineered cells of the invention may be unicellular organisms or may be derived from multicellular organisms. By "isolated" in reference to genetically engineered cells derived from multicellular organisms it is meant the cells are outside a living body, whether plant or animal, and in an artificial environment. The use of the term isolated does not imply that the genetically engineered cells are the only cells present.

In one embodiment, the genetically engineered cells of the invention contain any one of the nucleic acid constructs of the invention. In a second embodiment, an altered recombinase that specifically recognizes recombination sequences is introduced into genetically engineered cells containing one of the nucleic acid constructs of the invention under conditions such that the nucleic acid sequence(s) of interest will be inserted into the genome. Thus, the genetically engineered cells possess a modified genome. Methods of introducing polypeptides and DNA sequences into such cells are well known in the art and are discussed above.

The genetically engineered cells of the invention can be employed in a variety of ways. Unicellular organisms can be modified to produce commercially valuable substances such as recombinant proteins, industrial solvents, industrially useful enzymes, and the like. Preferred unicellular organisms include fungi such as yeast (for example, *S. pombe, Pichia pastoris, S. cerevisiae* (such as INVSc1), and the like) *Aspergillis*, and the like, and bacteria such as *Klebsiella, Streptomyces*, and the like.

Isolated cells from multicellular organisms can be similarly useful, including insect cells, mammalian cells and plant cells. Mammalian cells that may be useful include those derived from rodents, primates and the like. They include HeLa cells, cells of fibroblast origin such as VERO, 3T3 or CHOK1, HEK 293 cells or cells of lymphoid origin (such as 32D cells) and their derivatives. Preferred mammalian host cells include nonadherent cells such as CHO, 32D, and the like.

In addition, plant cells are also available as hosts, and control sequences compatible with plant cells are available, such as the cauliflower mosaic virus 35S and 19S, nopaline synthase promoter and polyadenylation signal sequences, and the like. Appropriate transgenic plant cells can be used to produce transgenic plants.

Another preferred host is an insect cell, for example from the *Drosophila larvae*. Using insect cells as hosts, the *Drosophila* alcohol dehydrogenase promoter can be used (Rubin, Science 240:1453–1459, 1988). Alternatively, baculovirus vectors can be engineered to express large amounts of peptide encoded by a desired nucleic acid sequence in insect cells (Jasny, Science 238:1653, (1987); Miller et al., In: Genetic Engineering (1986), Setlow, J. K., et al., eds., Plenum, Vol. 8, pp. 277–297)).

The genetically engineered cells of the invention are additionally useful as tools to screen for substances capable of modulating the activity of a protein encoded by a nucleic is acid fragment of interest. Thus, an additional embodiment of the invention comprises methods of screening comprising contacting genetically engineered cells of the invention with a test substance and monitoring the cells for a change in cell phenotype, cell proliferation, cell differentiation, enzymatic activity of the protein or the interaction between the protein and a natural binding partner of the protein when compared to test cells not contacted with the test substance.

A variety of test substances can be evaluated using the genetically engineered cells of the invention including peptides, proteins, antibodies, low molecular weight organic compounds, natural products derived from, for example, fungal or plant cells, and the like. By "low molecular weight organic compound" it is meant a chemical species with a molecular weight of generally less than 500–1000. Sources of test substances are well known to those of skill in the art.

Various assay methods employing cells are also well known by those skilled in the art. They include, for example, assays for enzymatic activity (Hirth, et al, U.S. Pat. No. 5,763,198, issued Jun. 9, 1998), assays for binding of a test substance to a protein expressed by the genetically engineered cells, assays for transcriptional activation of a reporter gene, and the like.

Cells modified by the methods of the present invention can be maintained under conditions that, for example, (i) keep them alive but do not promote growth, (ii) promote growth of the cells, and/or (iii) cause the cells to differentiate or dedifferentiate. Cell culture conditions are typically permissive for the action of the recombinase in the cells, although regulation of the activity of the recombinase may also be modulated by culture conditions (e.g., raising or lowering the temperature at which the cells are cultured). For a given cell, cell-type, tissue, or organism, culture conditions are known in the art.

G. Transgenic Plants and Non-Human Animals

In another embodiment, the present invention comprises transgenic plants and nonhuman transgenic animals whose genomes have been modified by employing the methods and compositions of the invention. Transgenic animals may be produced employing the methods of the present invention to serve as a model system for the study of various disorders and for screening of drugs that modulate such disorders.

A "transgenic" plant or animal refers to a genetically engineered plant or animal, or offspring of genetically engineered plants or animals. A transgenic plant or animal usually contains material from at least one unrelated organism, such as, from a virus. The term "animal" as used in the context of transgenic organisms means all species except human. It also includes an individual animal in all stages of development, including embryonic and fetal stages. Farm animals (e.g., chickens, pigs, goats, sheep, cows, horses, rabbits and the like), rodents (such as mice and rats), and domestic pets (e.g., cats and dogs) are included within the scope of the present invention. In a preferred embodiment, the animal is a mouse or a rat.

The term "chimeric" plant or animal is used to refer to plants or animals in which the heterologous gene is found, or in which the heterologous gene is expressed in some but not all cells of the plant or animal.

The term transgenic animal also includes a germ cell line transgenic animal. A "germ cell line transgenic animal" is a transgenic animal in which the genetic information provided by the invention method has been taken up and incorporated into a germ line cell, therefore conferring the ability to transfer the information to offspring. If such offspring, in fact, possess some or all of that information, then they, too, are transgenic animals.

Methods of generating transgenic plants and animals are known in the art and can be used in combination with the teachings of the present application.

In one embodiment, a transgenic animal of the present invention is produced by introducing into a single cell embryo a nucleic acid construct (e.g., a targeting construct), comprising a recombination site capable of recombining with a recombination site found within the genome of the organism from which the cell was derived and a nucleic acid fragment of interest, in a manner such that the nucleic acid fragment of interest is stably integrated into the DNA of germ line cells of the mature animal and is inherited in normal Mendelian fashion. In this embodiment, the nucleic acid fragment of interest can be any one of the fragments described previously. Alternatively, the nucleic acid sequence of interest can encode an exogenous product that disrupts or interferes with expression of an endogenously produced protein of interest, yielding transgenic animals with decreased expression of the protein of interest.

A variety of methods are available for the production of transgenic animals. A nucleic acid construct of the invention can be injected into the pronucleus, or cytoplasm, of a fertilized egg before fusion of the male and female pronuclei, or injected into the nucleus of an embryonic cell (e.g., the nucleus of a two-cell embryo) following the initiation of cell division (Brinster, et al., Proc. Nat. Acad. Sci. USA 82: 4438, 1985). Embryos can be infected with viruses, especially retroviruses, modified at a recombination site with a nucleic acid sequence of interest. The cell can further be treated with an altered recombinase as described above to promote integration of the nucleic acid sequence of interest into the genome. In this case, introducing the altered recombinase in the form of a mRNA may be particularly advantageous. There would then be no requirement for transcription of the incoming recombinase gene and no chance that the recombinase gene would become integrated into the genome.

By way of example only, to prepare a transgenic mouse, female mice are induced to superovulate. After being allowed to mate, the females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. See Hammer, et al., Cell 63:1099–1112, 1990). Rodents suitable for transgenic experiments can be obtained from standard commercial sources such as Charles River (Wilmington, Mass.), Taconic (Germantown, N.Y.), Harlan Sprague Dawley (Indianapolis, Ind.), etc.

The procedures for manipulation of the rodent embryo and for microinjection of DNA into the pronucleus of the zygote are well known to those of ordinary skill in the art (Hogan, et al., supra). Microinjection procedures for fish, amphibian eggs and birds are detailed in Houdebine and Chourrout, Experientia 47:897–905, 1991). Other procedures for introduction of DNA into tissues of animals are described in U.S. Pat. No., 4,945,050 (Sandford et al., Jul. 30, 1990).

Totipotent or pluripotent stem cells derived from the inner cell mass of the embryo and stabilized in culture can be manipulated in culture to incorporate nucleic acid sequences employing invention methods. A transgenic animal can be produced from such cells through injection into a blastocyst that is then implanted into a foster mother and allowed to come to term.

Methods for the culturing of stem cells and the subsequent production of transgenic animals by the introduction of DNA into stem cells using methods such as electroporation, calcium phosphate/DNA precipitation, microinjection, liposome fusion, retroviral infection, and the like are also are well known to those of ordinary skill in the art. (See, for example, Teratocarcinomas and Embryonic Stem Cells, A Practical Approach, E. J. Robertson, ed., IRL Press, 1987). Reviews of standard laboratory procedures for microinjection of heterologous DNAs into mammalian (mouse, pig, rabbit, sheep, goat, cow) fertilized ova include: Hogan et al., *Manipulating the Mouse Embryo* (Cold Spring Harbor Press 1986); Krimpenfort et al., 1991, *Bio/Technology* 9:86; Palmiter et al., 1985, Cell 41:343; Kraemer et al., *Genetic Manipulation of the Early Mammalian Embryo* (Cold Spring Harbor Laboratory Press 1985); Hammer et al., 1985, Nature, 315:680; Purcel et al., 1986, *Science*, 244:1281; Wagner et al., U.S. Pat. No. 5,175,385; Krimpenfort et al., U.S. Pat. No. 5,175,384, the respective contents of which are incorporated by reference.

The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene. Procedures for the production of non-rodent mammals and other animals have been discussed by others (see Houdebine and Chourrout, supra; Pursel, et al., Science 244:1281–1288, 1989; and Simms, et al., Bio/Technology 6:179–183, 1988). Animals carrying the transgene can be identified by methods well known in the art, e.g., by dot blotting or Southern blotting.

The term transgenic as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with loss of function that has been achieved by use of the invention vector. In one embodiment, transgenic animals having gene knockouts are those in which the target gene has been rendered nonfunctional by an insertion targeted to the gene to be rendered non-functional by targeting a pseudo-recombination site located within the gene sequence.

H. Gene Therapy and Disorders

A further embodiment of the invention comprises a method of treating a disorder in a subject in need of such treatment. In one embodiment of the method, at least one cell or cell type (or tissue, etc.) of the subject has a target recombination sequence for an altered recombinase of the present invention. This cell(s) is transformed with a nucleic acid construct (a "targeting construct") comprising a second recombination sequence and one or more polynucleotides of interest (typically a therapeutic gene). Into the same cell an altered recombinase is introduced that specifically recognizes the recombination sequences under conditions such that the nucleic acid sequence of interest is inserted into the genome via a recombination event. Subjects treatable using the methods of the invention include both humans and non-human animals. Such methods utilize the targeting constructs and altered recombinases of the present invention.

A variety of disorders may be treated by employing the method of the invention including monogenic disorders, infectious diseases, acquired disorders, cancer, and the like. Exemplary monogenic disorders include ADA deficiency, cystic fibrosis, familial-hypercholesterolemia, hemophilia, chronic ganulomatous disease, Duchenne muscular dystrophy, Fanconi anemia, sickle-cell anemia, Gaucher's disease, Hunter syndrome, X-linked SCID, and the like.

Infectious diseases treatable by employing the methods of the invention include infection with various types of virus including human T-cell lymphotropic virus, influenza virus, papilloma virus, hepatitis virus, herpes virus, Epstein-Bar virus, immunodeficiency viruses (HIV, and the like), cytomegalovirus, and the like. Also included are infections with other pathogenic organisms such as *Mycobacterium Tuberculosis, Mycoplasma pneumoniae*, and the like or parasites such as *Plasmadium falciparum*, and the like.

The term "acquired disorder" as used herein refers to a noncongenital disorder. Such disorders are generally considered more complex than monogenic disorders and may result from inappropriate or unwanted activity of one or more genes. Examples of such disorders include peripheral artery disease, rheumatoid arthritis, coronary artery disease, and the like.

A particular group of acquired disorders treatable by employing the methods of the invention include various cancers, including both solid tumors and hematopoietic cancers such as leukemias and lymphomas. Solid tumors that are treatable utilizing the invention method include carcinomas, sarcomas, osteomas, fibrosarcomas, chondrosarcomas, and the like. Specific cancers include breast cancer, brain cancer, lung cancer (non-small cell and small cell), colon cancer, pancreatic cancer, prostate cancer, gastric cancer, bladder cancer, kidney cancer, head and neck cancer, and the like.

The suitability of the particular place in the genome is dependent in part on the particular disorder being treated. For example, if the disorder is a monogenic disorder and the desired treatment is the addition of a therapeutic nucleic acid encoding a non-mutated form of the nucleic acid thought to be the causative agent of the disorder, a suitable place may be a region of the genome that does not encode any known protein and which allows for a reasonable expression level of the added nucleic acid. Methods of identifying suitable places in the genome are known in the art and identification of target recombination sequences is discussed herein in the context of the altered recombinases of the present invention.

The nucleic acid construct (e.g., a targeting vector) useful in this embodiment is additionally comprised of one or more nucleic acid fragments of interest. Preferred nucleic acid fragments of interest for use in this embodiment are therapeutic genes and/or control regions, as previously defined. The choice of nucleic acid sequence will depend on the nature of the disorder to be treated. For example, a nucleic acid construct intended to treat hemophilia B, which is caused by a deficiency of coagulation factor IX, may comprise a nucleic acid fragment encoding functional factor IX. A nucleic acid construct intended to treat obstructive peripheral artery disease may comprise nucleic acid fragments encoding proteins that stimulate the growth of new blood vessels, such as, for example, vascular endothelial growth factor, platelet-derived growth factor, and the like. Those of skill in the art would readily recognize which nucleic acid fragments of interest would be useful in the treatment of a particular disorder.

The nucleic acid construct can be administered to the subject being treated using a variety of methods. Administration can take place in vivo or ex vivo. By "in vivo," it is meant in the living body of an animal. By "ex vivo" it is meant that cells or organs are modified outside of the body, such cells or organs are typically returned to a living body.

Methods for the therapeutic administration of nucleic acid constructs are well known in the art. Nucleic acid constructs can be delivered with cationic lipids (Goddard, et al, Gene Therapy, 4:1231–1236, 1997; Gorman, et al, Gene Therapy 4:983–992, 1997; Chadwick, et al, Gene Therapy 4:937–942, 1997; Gokhale, et al, Gene Therapy 4:1289–1299, 1997; Gao, and Huang, Gene Therapy 2:710–722, 1995, all of which are incorporated by reference herein), using viral vectors (Monahan, et al, Gene Therapy 4:40–49, 1997; Onodera, et al, Blood 91:30–36, 1998, all of which are incorporated by reference herein), by uptake of "naked DNA", and the like. Techniques well known in the art for the transfection of cells (see discussion above) can be used for the ex vivo administration of nucleic acid constructs. The exact formulation, route of administration and dosage can be chosen by the individual physician in view of the patient's condition. (See e.g. Fingl et al., 1975, in "The Pharmacological Basis of Therapeutics", Ch. 1 pl).

It should be noted that the attending physician would know how to and when to terminate, interrupt, or adjust administration due to toxicity, to organ dysfunction, and the like. Conversely, the attending physician would also know how to adjust treatment to higher levels if the clinical response were not adequate (precluding toxicity). The magnitude of an administered dose in the management of the disorder being treated will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

In general at least 1–10% of the cells targeted for genomic modification should be modified in the treatment of a disorder. Thus, the method and route of administration will optimally be chosen to modify at least 0.1–1% of the target cells per administration. In this way, the number of administrations can be held to a minimum in order to increase the efficiency and convenience of the treatment.

Depending on the specific conditions being treated, such agents may be formulated and administered systemically or locally. Techniques for formulation and administration may be found in "Remington's Pharmaceutical Sciences," 1990, 18th ed., Mack Publishing Co., Easton, Pa. Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

The subject being treated will additionally be administered an altered recombinase that specifically recognizes the recombination sequences that are selected for use. The particular altered recombinase can be administered by including a nucleic acid encoding it as part of a nucleic acid construct, or as a protein to be taken up by the cells whose genome is to be modified. Methods and routes of administration will be similar to those described above for administration of a targeting construct comprising a recombination sequence and nucleic acid sequence of interest. The altered recombinase protein is likely to only be required for a limited period of time for integration of the nucleic acid sequence of interest. Therefore, if introduced as a gene encoding an altered recombinase, the vector carrying the altered recombinase gene will lack sequences mediating prolonged retention. For example, conventional plasmid DNA decays rapidly in most mammalian cells. The altered recombinase gene may also be equipped with gene expression sequences that limit its expression. For example, an inducible promoter can be used, so that altered recombinase expression can be temporally limited by limited exposure to the inducing agent. One such exemplary group of promoters are tetracycline-responsive promoters the expression of which can be regulated using tetracycline or doxycycline.

The invention will now be described in greater detail by reference to the following non-limiting Examples.

EXAMPLES

Example 1

A Thermally-Induced Screening Assay for Identifying Shuffled Recombinases

This assay uses two plasmids, called the resident plasmid (FIG. 1A) and the cloning plasmid (FIG. 1B). Construction of these plasmids was carried out as follows.

Resident plasmid. The temperature sensitive (TS) plasmid pTSK30 was used as the backbone for the final resident plasmid pTSK30 (Phillips, G. J., Plasmid 41:78–81 (1999)) was cut with DrdI and SmaI to remove the lacZ alpha gene. The DrdI end was made blunt with T4 polymerase, gel isolated, and re-ligated to a compatible SmaI blunt end resulting in the plasmid pTSK1st. A special linker that provided unique recognition sites was placed into this vector. This linker sequence was CGCGtggtgcttgcttagcgctagcg-catgc (Linker 1; SEQ ID NO:1). The CGCG sequence shown in capitals (i.e., the first four nucleotides) is a MluI overhang, whereas all other sequence represents double stranded DNA generated by complementary oligonucleotides. The pTSK1st plasmid was cut with Eco0109I and the ends made blunt with T4 polymerase so that it would be compatible with the blunt end of the linker. Once the Eco0109I end was made blunt, the plasmid was cut with MluI. The linker was ligated into the vector to make pTSK2nd.

An additional linker (Linker 2) was then added to the pTSK2nd plasmid to make pTSK3rd. The pTSK2nd plasmid was cut with MluI and BlpI to accept a customized linker in this position. The following complementary oligonucleotides were used to create Linker 2:
CGCGtgacgtcaaaaccggtgcggccgc-
gaattccggtccgaaacctaggaaactgcagggc gcgccaaagc (SEQ ID NO:2), and
TAAgctttggcgcgccctgcagtttc-
ctaggtttcggaccggaattcgcggccgcaccggtt ttgacgtca (SEQ ID NO:3). This linker introduced further unique restriction enzyme recognition sites. Bases shown in uppercase (SEQ ID NO:2, first four nucleotides and SEQ ID NO:3 first three nucleotides) represent the overhangs of the linker duplex pTSK4th was created by placing a PmeI recognition site into pTSK3rd pTSK3rd was cut with FspI to provide a position for the following blunt-ended PmeI linker (Linker 3). Linker 3 was generated by annealing the oligonucleotides ggggtttaaacggg (SEQ ID NO:4) and cccgtttaaacccc (SEQ ID NO:5).

pTSK5th was made by introducing the phage T5 promoter into pTSK4th. The T5 promoter was created from oligonucleotides
ctcataaaaaatttatttgctttcaggaaaattttctgtataatagattcataaatttgag agaggagtta (SEQ ID NO:6; T5 oligo 1) and
CCGGtaactcctctctcaaatttat-
gaatctattatacagaaaaattttcctgaaagcaaat aaatttttatgagACGT (SEQ ID NO:7; T5 oligo 2). pTSK4th was cut with the restriction enzymes AatII and AgeI, providing sites for directional ligation of the T5 promoter. A "stuffer sequence" was then added to pTSK5th. The stuffer acted as a spacer between the two attachment sites and to help prevent transcription read-through. The stuffer sequence was taken from a modified Promega (Madison, Wis.) plasmid called pGL3-CMV. pGL3-CMV was made by placing a CMV promoter in the SmaI site within the pGL3-Basic Promega plasmid. A 1.4 kb ApoI fragment from pGL3-CMV was placed in the compatible EcoRI site of pTSK5th to make pTSK6th.

A transcription terminator sequence was added to pTSK6th in the RsrII and AvrII sites, resulting in pTSK7th. The transcription terminator was made by annealing the complimentary oligonucleotides
GTCcgtggatttgttcagaacgctcggttgccgccgggcgttttttattggc (SEQ ID NO:8; transcription terminator oligo 1) and
CTAGgccaataaaaaacgcccggcg-
gcaaccgagcgttctgaacaaatccacg (SEQ ID NO:9; transcription terminator oligo 2), resulting in the terminator duplex with RsrII and AvrII overhangs. The pTSK8th plasmid received the GFPuv reporter gene in the SphI and NheI sites, which was later replaced with the full-length lacZ gene to provide greater sensitivity.

A temperature-sensitive mutant of the lac repressor gene (lacI TS) was introduced into pTSK8th at the PmeI site. The lacI TS promoter and gene sequence was removed from the plasmid pNH40lacIqTS (Hasan, N., Szybalski, W., Gene 163:35–40 (1995)) with EcoRI and made blunt to accommodate the PmeI ends on the pTSK8th vector which resulted in the plasmid pTSK9th. A 59 bp wild-type φC31 attP site (ggagtagtgccccaactggggtaac-
ctTTGagttctctcagttgggggcgtagggtcgc, FIG. 1C, SEQ ID NO:33, the TTG core is in upper case) was placed into pTSK9th's unique NotI restriction site resulting in the plasmid pTSK9th(attP-NotI). The GFPuv gene in this plasmid was replaced by the full-length lacZ gene to give p10th(attP-NotI).

To enhance the expression of lacZ, a Shine-Delgarno and Kozac sequence were introduced by PCR upstream of the ATG translation starting position. The lacZ PCR primers also introduced restriction enzyme sites NheI and SphI so that the lacZ fragment could conveniently replace the GFPuv gene found in the previous generation plasmid. The φC31 attB site was added into the unique AscI site of p10th(attP-NotI) to give the plasmid p11th-PB. An attB site was made from the following oligonucleotides
CGCGcctgcgggtgccagggcgtgccct-
tgggctccccgggcgcgtactccgg (SEQ ID NO:10; attB oligo 1) and
CGCGccggagtacgcgcccggggagc-
ccaagggcacgccctggcacccgcagg (SEQ ID NO:11; attB oligo 2).

The stuffer sequence in this plasmid was then replaced with a sequence that would better reduce the amount of lacZ background. In order to perform the sequence replacement, the original stuffer sequence was removed. FseI and RsrII were used to remove most of this sequence, while making the remaining PstI site unique to this vector. The ends were made blunt by T4 polymerase and religated to give the plasmid pΔPB. The primers CGTTGGGACCCGTTTC-CGTG (SEQ ID NO:12; primer 1) and AGAGACGAG-GAGAGGGGAGC (SEQ ID NO:13; primer 2) were used to perform PCR from human genomic DNA. A PCR using this primer set produced a 2.3 kb GC-rich fragment from an intron of the human FGFR3 gene. Immediately internal to these primers are PsI sites. The PCR product was cut with PstI and ligated into the unique PstI site present in pΔPB, resulting in the plasmid pPB(+) stuffer(+). Only one orientation of this stuffer sequence was able to prevent background expression.

A similar version of this plasmid was made by replacing the wild-type attP with the pseudo-site A (ψA) sequence from the human genome (FIG. 13; SEQ ID NO:34). The ψA was isolated from the human genome by PCR using the primers ATTTGTAGAACTATTATGGG (SEQ ID NO:14; psiA primer 1) and AAGTCTTCTGGCTATACAGG (SEQ ID NO:15; psiA primer 2). The approximately 470-bp ψA was then cloned into pCR2.1 topo (Invitrogen). The ψA site was removed with XbaI and SpeI and cloned into the SpeI site of pBC-PB (Groth, et al., Proc. Natl. Acad. Sci. 97:5995–6000 (2000)), resulting in the plasmid pBC-psEcol-B (+). The EcoRI fragment containing ψA from this plasmid was removed and made blunt with T4 polymerase. To remove the wild-type attP site from the pPB(+) stuffer(+) plasmid so that it could be replaced with ψA, the plasmid was cut with SacII and AvrII and made blunt. The blunted ψA-EcoRI fragment was ligated into this position resulting in the plasmid pRES-psA.

Cloning plasmid. The pINT plasmid (Groth, et al., Proc. Natl. Acad. Sci. 97:5995–6000 (2000)) was modified for use in this assay. To first make the vector tetracycline resistant (TcR), pINT was cut with DraIII and PflMI and made blunt with T4 polymerase. This step provided a position for the TcR gene and also removed the kanamycin resistance (KanR) gene from the pINT vector. From pBR322, the TcR gene was removed with EcoRI and PflMI, made blunt, and used to replace the KanR gene, resulting in the plasmid pINT-Tc $2^{nd}$ (+) A plasmid called pREC was created from pINT-Tc $2^{nd}$(+) by placing in a linker in place of the integrase gene. The pINT-Tc $2^{nd}$(+) plasmid was cut with BstEII and SpeI, which removed the integrase gene. A linker (Linker 4) created with the oligonucleotides
GTCACgctcgagagatctga (SEQ ID NO:16; linker 4, first oligo) and CTAGtcagatctctcgagc (SEQ ID NO:17; liner 4, second oligo) was placed into these sites, which introduced unique restriction enzyme sites to the plasmid (BglII and XhoI).

A mutant integrase library could now be moved in and out of the vector without disrupting the plasmid, because unique sites flank the integrase gene. The wild-type φC31 integrase gene was re-introduced into the pREC plasmid to generate the pINT-CRS plasmid. This step was done by removing integrase from the pINT-Tc $2^{nd}$(+) plasmid with BamHI and SpeI. The pREC plasmid was cut with BglII and SpeI to accept the integrase gene in this position. The ligation reaction was possible because BglII and BamHI ends are compatible with each other. XhoI and SpeI sites are unique to the pINT-CRS vector and can be used to shuttle an integrase library to and from the vector.

Performing the Assay.

The resident and cloning plasmids described above were used in an assay system developed for identifying evolved, improved integrases. The screen allows the isolation of altered recombinases (e.g., integrases) that now show improved recombination efficiency towards wild-type or pseudo-att site sequences. The efficiency of an improved integrase for recombining any pair of att sites can be determined in this assay and is measured by screening for colonies that produce more lacZ gene product, the enzyme β-galactosidase. The resident plasmid only expresses β-galactosidase after an integrase-mediated intramolecular integration event has occurred. Without this recombination event, the resident plasmid is configured with a "stuffer sequence" containing transcription termination signals separating the att sites. Directly upstream of the attachment site sequences resides a strong bacterial promoter. Downstream of the att sites and stuffer sequence is the lacZ gene. In the event of recombination, the stuffer sequence is removed and the promoter mediates the transcription of lacZ, producing β-galactosidase. β-galactosidase production can be conveniently detected by growing bacteria on plates containing the indicator dye X-gal (Miller, J. H., Experiments in Molecular Genetics, 1972).

To perform the assay, bacteria carrying the resident plasmid were made competent for transformation. The resident plasmid was kanamycin resistant (KanR) and used a variant of the pSC101 backbone for replication. In this variant, the pSC101 backbone had a mutation in the RepA gene rendering it temperature sensitive. The resident plasmid also carried the att sites of choice (in this example, attB, FIG. 11B, and ψA FIG. 13), lacZ, and a temperature sensitive lacI gene. Bacteria carrying this plasmid grew normally at 30° C., but did not grow at 42° C. because of the TS mutant RepA. Similarly, the TS lacI produced lac repressor that was fully functional at 30° C., but inactive at 42° C. Both of the TS components act in an intermediate temperature sensitive manner at intermediate temperatures. For example, bacteria carrying the TS plasmid did not cease to grow at 37° C., but the amount of growth was significantly reduced. In the same manner, the TS lac repressor was not completely inactive at 37° C., but it was not stable enough to cause complete repression of the lac promoter/operator. Because the φC31 integrase loses stability at higher temperatures, 37° C. was used as the induction temperature; however, it is possible to screen for integrase mutants that perform well at 42° C.

The second plasmid (the cloning plasmid) used in this system carried the shuffled integrase library. This cloning plasmid was tetracycline resistant (TcR) and contained the p15A origin of replication. Both plasmids of the system had compatible origins and therefore can be propagated together in the same bacterial cell. To complete the cloning plasmid, a shuffled integrase library was ligated into the unique XhoI and SpeI restriction sites that were positioned immediately downstream of the lac promoter/operator. The cloning plasmid carrying the shuffled library was then transformed into bacteria carrying the resident plasmid.

The shuffling of the integrase gene was performed similarly to published protocols (Stemmer, W. P. C., Proc. Natl. Acad. Sci. USA 91, 10747–10751 (1994); Stemmer, W. P. C., Nature 370, 389–391 (1994)). Briefly, the φC31 integrase gene (the coding region DNA sequence is presented as SEQ ID NO:20, FIG. 4) was copied from the pINT-CRS vector by PCR with the primers CTAAAGGGAACAAAAGCTGGAG (SEQ ID NO:18; phiC31 primer 1) and TGATATGGGGCAAATGGTGGTC (SEQ ID NO:19; phiC31 primer 2). These primers lie directly adjacent to the unique XhoI and SpeI restriction sites, which were used to clone the shuffled library back into the vector. Five micrograms of integrase gene were treated with 2.4 U of DNAse for 25 minutes at room temperature. Fragments of the integrase gene were run out on a 1.6% NuSieve gel in 1×TAE. Fragments in the range of approximately 50 bp–250 bp long were cut out of the gel. DNA fragments were removed from the low-melt gel with beta-agarase. Forty-five cycles of primer-less extensions were performed as described (Stemmer, W. P. C., Proc. Natl. Acad. Sci. USA 91, 10747–10751 (1994); Stemmer, W. P. C., Nature 370, 389–391 (1994)). To amplify the shuffled integrase library, a portion of the primer-less reaction was added to the primers shown above, and further PCR was performed. A portion of the resulting PCR product was analyzed by gel electrophoresis. The expected size of 1.9 kb was obtained, although minor additional bands were observed. To increase the likelihood of creating a library carrying only the full-length shuffled integrase gene and not truncated products from inefficient PCR, gel isolation of the final product was performed. The integrase gene library was cut with the restriction enzymes XhoI and SpeI and ligated into the source cloning vector devoid of the integrase gene. Ligation reactions used to produce the plasmid library were cleaned with MinElute Qiagen columns (Qiagen, Valencia, Calif.) and transformed into electro-competent DH10B bacteria (Life Technologies) carrying the resident plasmid pRES-ψA described above, which bears the wild type attB site and the ψA pseudo attP site derived from the human genome (FIG. 13).

After transformation, cells were allowed to recover in medium for 1 hour and 20 minutes at 30° C. Expression of the integrase was repressed upon transformation because of the high levels of the lac repressor expressed from the resident plasmid. Because the integrase gene was under the control of the lac promoter/operator, it was under continuous repression unless activated by an elevated temperature. As long as the cells were maintained at 30° C., integrase expression remained turned off, both cloning and resident plasmids replicated, and the bacteria grew normally. Transformants were grown on agar plates containing tetracycline, kanamycin, and X-gal. The transformation was plated to give ≦150 colonies per 100-mm plate to allow for optimal growth and screening.

Colonies were permitted to grow at 30° C. for 26–33 hours to produce large colonies. Plates were then moved to 37° C. for an induction period. During this time, the TS lac repressor became less active, allowing the expression of integrase. In addition, colony growth was slowed due to the TS replication mutant on the resident plasmid. Since the bacteria were under double antibiotic selection, only those cells carrying both plasmids survived. Depending on the activity of the integrase towards the att sites on the resident plasmid, different amounts of time at 37° C. were required to assay for an improved integrase.

Exemplary Results of the Assay

The screening assay and vectors described above were used to find evolved φC31 integrase genes that mediated more efficient recombination between attB and the ψA pseudo attP sequence derived from the human genome. The φC31 integrase gene was subjected to one round of DNA shuffling as described above, and the shuffled set of fragments was ligated into the cloning plasmid. The plasmid library of shuffled integrases was transformed into DH10B bacteria carrying pRES-psA (the resident plasmid, described above) and the screening assay was performed.

Transformant colonies were grown on plates at 30° C. until moderately large colonies were obtained. The plates were then moved to 37° C. for 24 hours to inactivate the TS lacI, allowing expression of the integrase gene encoded by the cloning plasmid. Mutant integrases capable of efficiently recombining the test att sites excise the stuffer sequence and allow transcription of lacZ on the resident plasmid. Plates were then moved to room temperature overnight. This period allowed time for β-galactosidase to cleave the X-gal substrate in the plates, necessary to generate blue color in the colonies. Colonies were then scored by eye for increased blueness. Several bluer colonies were obtained from screening approximately 1,000 colonies. Plasmid DNAs from three such colonies, designated mutants 1C1, 5C1, and 7C1, were purified and used for DNA sequence and functional analysis. The mutants were assigned numbers followed by "C1," indicating that the mutants were obtained from a library that underwent one cycle of shuffling.

Following the above procedures using the φC31 recombinase (parent, wild-type DNA sequence presented as SEQ ID NO:20, FIG. 4; parent, wild-type protein sequence presented as SEQ ID NO:21, FIGS. 3A and 3B) three altered recombinases were identified 1C1, 5C1, and 7C1. An alignment of the protein sequences of the wild-type and altered recombinases is presented in FIGS. 3A and 3B. In FIGS. 3A and 3B, the protein sequence for altered recombinase 7C1 (SEQ ID NO:22), wild-type recombinase φC31 (SEQ ID NO:21), altered recombinase 5C1 (SEQ ID NO:23), and altered recombinase 1C1 (SEQ ID NO:24), are presented relative to a consensus sequence (SEQ ID NO:25). The asterisk at the ends of the sequences in FIGS. 3A and 3B represents a stop codon. FIG. 5 (SEQ ID NO:22) and FIG. 6 (SEQ ID NO:26) present, respectively, the peptide and DNA sequences of altered recombinase 7C1. FIG. 7 (SEQ ID NO:23) and FIG. 8 (SEQ ID NO:27) present, respectively, the peptide and DNA sequences of altered recombinase 5C1. FIG. 9 (SEQ ID NO:24) and FIG. 10 (SEQ ID NO:28) present, respectively, the peptide and DNA sequences of altered recombinase 1C1.

As discussed above, these altered recombinases may be used in further rounds of screening using the methods of the present invention.

The following provides a summary of the DNA sequence changes present in each of the mutant integrases (i.e., altered recombinases) relative to the wild-type sequence:

```
1C1 mutant:

225 bp  (G->A)         silent 511 bp  (T->C)         silent 1135 bp  (G->A)         (aa379) Valine[V] ->Isoleucine[I]

1509 bp  (A->G)         silent 1707 bp  (C->T)         silent 1810 bp  (C deletion)   Created the new reading frame: (605) Arg- (606) Thr- (607) Ala- (608) Arg- (609) Lys- (610) Thr-* {Versus the wild-type sequence:

(605) Gln- (606) Asp- (607) Gly- (608) Thr- (609) Gln- (610) Asp- (611) Val- (612) Ala- (613) Ala-*}

5C1 mutant:

171 bp  (G->A)         silent 736 bp  (G->A)         (aa246) Alanine[A] ->Threonine[T]

1109 bp  (A->G)         (aa370) Aspartic acid[D] ->Glycine[G]

1788 bp  (G->A)         silent
```

-continued

```
7C1 mutant:

882 bp  (T->C)      silent 1678 bp  (G->A)      (aa560) Valine[V]       ->Methionine[M]

1825 bp  (G->C)      (aa609) Glutamic acid[E] ->Glutamine[Q]
```

To roughly quantify the relative improvements in substrate recognition for the mutant integrases acquired from the first round of shuffling, they were individually tested in a time course assay. The plasmids pREC, pINT-CRS, p1C1, p5C1, and p7C1 were transformed into the DH10b strain carrying the resident plasmid pRES-psA and grown for 33 hours at 30° C. Plasmids pREC and pINT-CRS were controls, constituting the cloning plasmid either not carrying an integrase gene or carrying the wild-type φC31 integrase gene, respectively. The three mutants, 1C1, 5C1, and 7C1, were also carried in the cloning plasmid. After the colonies were fully grown, plates were placed 37° C. to reduce the activity of the temperature sensitive proteins. As a non-induced control, one plate per group was not subjected to the higher temperature and was incubated at room temperature throughout the course of the experiment. Colonies were scored for blueness without temperature induction of integrase expression at 37° C. and again after periods of 37° C. incubation ranging between 16 and 39 hours. At the time of analysis, colonies were scored as being blue if they contained at least small areas of blue color.

The results of this time course analysis were as follows. The pREC control failed to give blue colonies at any of the time points, as expected, because this plasmid does not contain an integrase gene. pINT-CRS, carrying the wild-type integrase, produced low levels of recombination, reflected by the presence of blue in some of the colonies. With 16–39 hours of induction at 37° C., 10–30% of the pINT-CRS colonies contained some blue areas. Although longer induction times resulted in a higher percentage of colonies with blue areas, the amount of blue per colony was small and was relatively similar between the time points. By comparison, the 1C1 mutant generated blue areas in nearly 100% of the colonies with a 16 hour incubation at 37° C. For this mutant, increasing the amount of time at 37° C. did not increase the number of blue colonies, but did increase the amount of blue present within the colonies. The areas of blue present within colonies steadily increased with increased induction time at 37° C. The 5C1 mutant integrase performed slightly less efficiently compared to the 1C1 mutant. With 16 hours at 37° C., approximately 70% of the colonies contained areas of blue, reaching 100% with 24 hours of induction. Ratios of blue to white colonies increased with induction times, as did the amount of blue within a colony. The 7C1 mutant performed similarly to the wild-type integrase. This mutant was apparently not significantly improved over the wild type, but was a variant that looked bluer on the original screening plate. This result is possible, because the wild-type integrase has a residual level of activity towards ψA. Picking mutants like 7C1 can be avoided by reducing the induction time, thereby creating a more stringent screen for improved genes.

These results demonstrate the ability of the method of the present invention to produce evolved recombinases starting with parent recombinase (e.g., φC31 integrase). Such altered recombinases can be selected that mediated more efficient recombination between, for example, attB and a genomic site in a target organism (e.g., the ψA pseudo attP sequence derived from the human genome). The nucleic acid coding sequences of such altered recombinases typically differ from the coding sequences of their parent recombinase(s) by at least one base pair, typically giving rise to at least one amino acid difference in the polypeptide coding sequences of the altered recombinases relative to the parent. Further, coding sequence variations identified in different altered recombinases may be combined into a coding sequence for a single altered recombinase.

Example 2

Assaying Altered Integrases in Mammalian Cells

The screening assay for improved integrases was performed in E. coli. The altered integrases emerging from this screen can be tested in other species to determine if the desirable properties detected in bacteria are retained. The wild-type φC31 integrase and the 1C1 integrase mutant described in Example 1 were compared to each other in mammalian tissue culture cells for their ability to mediate the integration of a plasmid carrying the attB recognition site (FIG. 11B; SEQ ID NO:30) and the neomycin resistance gene into human chromosomes. Efficiencies of the integrases were determined by evaluating the number of neomycin resistant colonies formed after G418 selection.

The 293 human embryonic kidney cell line was used for these experiments (Graham, F. L., et al., J. Gen. Virol. 36, 59–72 (197.7)). Cells were grown to 50–80% confluency in 60-mm-diameter dishes and transfected with 50 ng of the donor attB neo plasmid pNC-attB and 5 µg of pCMVInt (Groth, A. C., et al., Proc. Natl. Acad. Sci. USA 97, 5995–6000 (2000)), pCMV-1C1, or pCMVSPORTβGal (Life Technologies, Gaithersburg Md.) by using Lipofectamine (Life Technologies). pNC-attB was a plasmid comprising (in the following order) a CMV promoter, the φC31 attB sequence (FIG. 11B, SEQ ID NO:30), sequences coding a neomycin resistance gene, and sequence coding a green florescence protein gene. pCMV-1C1 is identical to pCMVInt, except in place of the wild-type φC31 integrase gene, it carries the 1C1 mutant integrase under the control of the CMV promoter. The pCMVSPORTβGal negative control plasmid has no integrase gene. Twenty-four hours after transfection, the cells were transferred onto 100-mm-diameter dishes and grown for an additional 24 hours before medium was replaced with medium containing Geneticin at 350 µg/ml (G418, a neomycin analog; Life Technologies). Typically, 5 µg of DNA was near the upper limit for transfection of 60-mm-diameter dishes of 293 cells without appreciable toxicity.

Selection was continued for 14 days, then individual neomycin resistant colonies were counted. When pCMVSPORTβGal, which lacks an integrase gene, was co-transfected with pNC-attB, some neomycin resistant colonies were obtained and were considered the background due to random integration. Co-transfections of pNC-attB with pCMVInt and pCMV-1C1 both resulted in increases in colony numbers above background of more than 10-fold. Furthermore, we found that plates transfected with pCMV-1C1 gave two-fold more colonies than those transfected with pCMVInt bearing the wild-type integrase plasmid. This experiment was repeated twice with similar results.

These results demonstrate that the altered 1C1 integrase mutant that resulted from DNA shuffling and was detected using the screening assay described in Example 1, also functions well in mammalian cells. The mutant integrase mediates efficient integration into the genome, performing genomic modification at a similar or higher frequency than the wild-type integrase. Integration specific for the ψA site was demonstrated by analyzing individual neomycin resistant colonies by PCR. For this assay a primer specific for the integration junction between the donor pNC-attB plasmid and the human genomic DNA in the vicinity of ψA was used.

Example 3

Additional Methods for Identifying Altered Recombinases

Below are four additional schemes that are useful in different situations to identify desired altered recombinase from a shuffled library of a recombinase gene, prepared, e.g., as outlined in Example 1.

A. A Chromosomal Method for Identifying Altered Recombinases.

An additional scheme to find recombinase variants with altered specificities involves integration of an assay plasmid carrying a pseudo attB site into the E. coli chromosome at an inserted attP site. Integration results in activation of transcription of a lacZ gene, which is detected with the fluorescence-activated cell sorter. Shuffled recombinase genes are transformed into the assay strain and subjected to sorting on a fluorescence-activated cell sorter. Plasmids from the highest expressing cells are used as the source of recombinase fragments for the next round of shuffling, followed by repetition of the assay. This provides a progressive approach to an enzyme with optimal specificity for the selected pseudo att sequence.

This assay can also be performed with an attP plasmid integrating into a chromosomally-inserted attB site.

B. Kanamycin Selection Scheme for Detecting Improved Recombinases.

In order to detect activity of a shuffled recombinase on substrate (i.e., selected) att sites for which the wild-type enzyme shows little or no activity, the following bacterial selection scheme can be used. On the assay plasmid, the two att sites between which recombination is desired are placed on a plasmid flanking a promoterless antibiotic resistance gene, in this case a kanamycin resistance gene. The att sites are in an inverted orientation, so that when recombination occurs, the kanamycin gene is flipped around and placed under the control of a bacterial promoter (e.g., the lacZ promoter). In order to ensure that the recombination occurs between the two att sites, a transcription terminator may be placed downstream of the second att site.

Libraries of plasmids containing shuffled recombinases are then transformed into bacteria containing this assay plasmid. If the transformed bacteria grow on kanamycin, a recombination event has occurred between the two attachment sites. If the starting recombinase does not recognize the test att site at all, then growth on kanamycin indicates an improvement in recombination frequency at the desired att site. If the starting recombinase causes recombination between the test att sites very slowly, then an improved enzyme is indicated by growth on kanamycin after only a short time is allowed for recombination to occur.

The assay is used in two ways. After transformation and incubation without kanamycin for a set amount of time (for example, six hours) the bacteria are plated, and any colonies that form result from a recombination event. Alternatively, the entire transformed library is grown in liquid culture, to which kanamycin is added at a set time, and then grown overnight. In either case, DNA is prepared from the cells that grow in the presence of kanamycin and used in the next round of shuffling. As progressively improved enzymes are found, the incubation time before addition of kanamycin is decreased.

C. Two Plasmid FACS Assay for Detection of Recombinases Improved for Recombination at Sites on which they are Already Active.

In order to detect increased activity of a shuffled recombinase on an att site that the wild type enzyme already recognizes efficiently (for example, a wild type att site), a FACS (Fluorescence Activated Cell Sorter)-based bacterial screen is used. The recombination event measured by the assay is a cassette exchange that results in the expression of a marker gene, for example, green fluorescent protein (GFP), that is detectable by FACS. The bacteria contain a resident high copy number plasmid with a DH origin of replication (Phillips, G. J., et al., BioTechniques 28, 400–408 (2000)) that contains a promoterless marker gene (GFP) flanked by two att sites in the same orientation (in this example, attp's). A transcriptional terminator is placed upstream of the entire cassette, to ensure a lack of GFP expression. The incoming plasmid library, in which the shuffled recombinases are cloned, bears a compatible high copy number plasmid with a ColE1 origin. The plasmid carrying the recombinase library also contains two att sequences (in this example attB's) in the same orientation as the attPs, flanking a filler sequence approximately the same size as the GFP gene. The attP and attB plasmids are approximately the same size. Upstream of the first attB is a promoter (in this case a lacZ promoter). If recombination occurs between an attB and an attP, an intermediate plasmid is created with two attB/attP hybrid att sites, an attB, and an attP. φC31 recombinase rapidly resolves such a plasmid into two separate plasmids, by recombination between attB and attP. If the initial recombination occurs between the first attB and the first attP or the second attB and the second attp, the final products include a plasmid that contains the recombinase and a GFP gene that is now being driven by the lacZ promoter. The more recombination events that occur in a cell (i.e., the better the integration frequency), the more GFP is expressed.

Bacteria that express a high amount of GFP are sorted out of the population by FACS and grown up. DNA is recovered from these bacteria.

In this assay, half of the events do not result in the expression of GFP (if the first attB recombines with the second attp, or vice versa). In order to lower this fraction of the population, shortened attachment sites are substituted for the second attB and second attp sequence. There is a greater integration frequency between full length att sites than between a 35 bp attB and a full-length attP (Groth, A. C., et al., Proc. Natl. Acad. Sci. USA 97, 5995–6000 (2000)). No such preference has been demonstrated for the excision reaction.

D. SacB Selection Scheme and In Vitro Assay of Improved Shuffled Recombinases.

A single plasmid selection scheme for functional recombinases utilizes the negative selectable marker gene sacB from *Bacillus subtilus*. In the presence of sucrose, the sacB gene product incorporates sucrose monomers into polymers that interfere with the normal structure of the *E. coli* cell wall causing lysis (Quandt, J., and Hynes, M. F. Gene 127, 15–21 (1993)). A constitutively expressed sacB gene is flanked by recombinase att sites oriented in such a manner than a site-specific recombination reaction excises the sacB gene from the plasmid, resulting in a sucrose resistant colony. Without recombination, this plasmid kills bacteria in the presence of sucrose.

Shuffled recombinase DNA fragments are ligated into the selection plasmid downstream of a T7 promoter, and the resultant plasmid library is transformed into *E. coli* bacteria containing a regulatable T7 RNA polymerase cassette. Altered recombinase proteins are expressed in most cells receiving a plasmid, but only cells carrying plasmids whose recombinases can recombine the att sites flanking the sacB survive once the cells are grow in sucrose containing media.

To quantify and compare the activities of these functional recombinases, a high-throughput in vitro recombination assay is combined with the above selection scheme. Surviving bacteria (either as single colonies or pools of clones) are picked and grown in a 96-well format for protein production. Large amounts of protein are produced utilizing the high activity of the T7 RNA polymerase on its promoter. Cells in each well of the 96-well plate are harvested and lysed, releasing a crude protein extract containing mutant recombinase protein (i.e., altered recombinase). The mutant proteins are purified quickly in the 96-well format via a N-terminal 6x-histidine tag introduced into all the mutant proteins at the time of shuffling. These purified proteins are then incubated with known quantities of linear DNA fragments encoding the test att sites under conditions that favor recombinase catalyzed recombination. Reaction products are directly analyzed on agarose gels and the extent of the reaction quantified using a densitometry software package. The best performing shuffled recombinases are retained and used in subsequent rounds of DNA shuffling.

Example 4

Family Shuffling for Identifying Altered Recombinases

To further increase the benefit of shuffling in creating altered recombinase enzymes, a strategy known as family shuffling can also be employed. In this approach, instead of using just one parent gene encoding a recombinase for the shuffling reaction, two or more homologous genes are simultaneously shuffled. By this method a more varied mixture is obtained that will patch together segments from the different genes to create more divergent variants. This approach has proven to be more effective than single gene shuffling. For example, altered enzymes were made by mixing four cephalosporinase genes from diverse species (Crameri, A., et al., Nature 391, 288–291 (1998)). In this example, this process was 50-fold more effective than single gene shuffling. Another example shuffled two thymidine kinase genes (Christians, F. C., et al., Nature Biotechnology 17, 259–264 (1999)) and achieved impressive results.

In the case of recombinase shuffling, family shuffling is done by mixing the genes for several evolutionarily related phage integrase genes, for example, the φC31, R4, and TP901 integrase genes. Assays such as those described herein are then used to screen variants for altered recombinase specificity and efficiency. The attP and/or attB sequences may be selected based on homologies to one or more of attP and/or attB sites of the selected integrase genes. Further, related attP and/or attb sequences obtained from target genomes (such as humans or mice) may be used to construct resident plasmids for use in this method.

While the foregoing has been with reference to particular embodiments of the invention, it will be appreciated by those skilled in the art that changes in these embodiments may be made without departing from the principles and spirit of the invention, the scope of which is defined by the appended claims.

What is claimed is:

1. A method of site-specifically integrating a nucleic acid into a genome of a cell of a multicellular non-human animal, said method comprising:

introducing a targeting vector comprising said nucleic acid and a vector attachment site and an altered, unidirectional site-specific bacteriophage integrase into a cell and maintaining said cell under conditions sufficient for said vector to integrate into said genome of said cell by a recombination event mediated by said altered unidirectional site-specific bacteriophage integrase, wherein said unidirectional site-specific bacteriophage integrase is at least 80% identical to SEQ ID NO:21 and has integrase activity.

2. The method according to claim 1, wherein said cell is present in vitro.

3. The method according to claim 1, wherein said cell is present in vivo.

4. The method according to claim 1, wherein said nucleic acid comprises a coding sequence.

5. The method according to claim 4, wherein said coding sequence is present in an expression cassette.

6. The method according to claim 1, wherein said genome attachment site is a pre-selected site in said genome.

7. The method according to claim 1, wherein said nucleic acid comprises a control region.

8. The method according to claim 7, wherein said control region is a promoter.

9. The method according to claim 1, wherein said cell is a mammalian cell.

10. A method of site-specifically integrating a nucleic acid into a genome of a mammalian cell of a multicellular organism, said method comprising:

introducing a targeting vector comprising said nucleic acid and a vector attachment site and an altered, unidirectional site-specific bacteriophage integrase into a cell present in vitro and maintaining said cell under conditions sufficient for said vector to integrate into said genome of said cell by a recombination event mediated by said altered unidirectional site-specific bacteriophage integrase, wherein said unidirectional site-specific bacteriophage integrase is at least 80% identical to SEQ ID NO:21 and has integrase activity.

11. The method according to claim 10, wherein said nucleic acid comprises a coding sequence.

12. The method according to claim 11, wherein said coding sequence is present in an expression cassette.

13. The method according to claim 10, wherein said genome attachment site is a pre-selected site in said genome.

14. The method according to claim 10, wherein said nucleic acid comprises a control region.

15. The method according to claim 14, wherein said control region is a promoter.

16. The method according to claim 10, wherein said cell is a human cell.

17. A method of site-specifically integrating a nucleic acid into a genome of a cell of a multicellular non-human animal, said method comprising:

introducing a targeting vector comprising said nucleic acid and a vector attachment site and an altered, unidirectional site-specific bacteriophage integrase into a cell present in vivo and maintaining said cell under conditions sufficient for said vector to integrate into said genome of said cell by a recombination event mediated by said altered unidirectional site-specific bacteriophage integrase, wherein said unidirectional site-specific bacteriophage integrase is at least 80% identical to SEQ ID NO:21 and has integrase activity.

18. The method according to claim 17, wherein said nucleic acid comprises a coding sequence.

19. The method according to claim 18, wherein said coding sequence is present in an expression cassette.

20. The method according to claim 17, wherein said genome attachment site is a pre-selected site in said genome.

21. The method according to claim 17, wherein said nucleic acid comprises a control region.

22. The method according to claim 21, wherein said control region is a promoter.

23. The method according to claim 1, wherein said unidirectional site-specific bacteriophage integrase is at least 90% identical to SEQ ID NO:21 and has integrase activity.

24. The method according to claim 1, wherein said unidirectional site-specific bacteriophage integrase is at least 95% identical to SEQ ID NO:21 and has integrase activity.

25. The method according to claim 10, wherein said unidirectional site-specific bacteriophage integrase is at least 90% identical to SEQ ID NO:21 and has integrase activity.

26. The method according to claim 10, wherein said unidirectional site-specific bacteriophage integrase is at least 95% identical to SEQ ID NO:21 and has integrase activity.

27. The method according to claim 17, wherein said unidirectional site-specific bacteriophage integrase is at least 90% identical to SEQ ID NO:21 and has integrase activity.

28. The method according to claim 17, wherein said unidirectional site-specific bacteriophage integrase is at least 95% identical to SEQ ID NO:21 and has integrase activity.

* * * * *

UNITED STATES PATENT AND TRADEMARK OFFICE
Certificate

Patent No. 7,141,426 B2                                    Patented: November 28, 2006

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Michele P. Calos, Burlingame, CA (US) and Christopher R. Sclimenti, La Jolla, CA (US).

Signed and sealed this Eighth Day of June 2010.

CHRISTOPHER S. F. LOW
*Supervisory Patent Examiner*
Art Unit 1636

UNITED STATES PATENT AND TRADEMARK OFFICE
CERTIFICATE OF CORRECTION

| | |
|---|---|
| PATENT NO. | : 7,141,426 B2 |
| APPLICATION NO. | : 10/836323 |
| DATED | : November 28, 2006 |
| INVENTOR(S) | : Michele Pamela Calos |

Page 1 of 1

It is certified that error appears in the above-identified patent and that said Letters Patent is hereby corrected as shown below:

In the specification
In column 1, lines 12-16, please replace the government rights statement to read --This invention was made with Government support under contracts DK058187 and DK055569 awarded by the National Institutes of Health. The Government has certain rights in the invention--.

Signed and Sealed this
Twenty-fourth Day of May, 2016

Michelle K. Lee
*Director of the United States Patent and Trademark Office*